United States Patent [19]
Della Valle et al.

[11] Patent Number: 5,990,170
[45] Date of Patent: Nov. 23, 1999

[54] THERAPEUTIC USE OF MONO AND BICARBOXYLIC ACID AMIDES ACTIVE AT THE PERIPHERAL CANNABINOID RECEPTOR

[75] Inventors: Francesco Della Valle; Alberta Leon; Gabriele Marcolongo; Silvana Lorenzi, all of Padua, Italy

[73] Assignee: Lifegroup S.p.A., Monselice, Italy

[21] Appl. No.: 08/860,356

[22] PCT Filed: Dec. 13, 1995

[86] PCT No.: PCT/EP95/04927

§ 371 Date: Sep. 30, 1997

§ 102(e) Date: Sep. 30, 1997

[87] PCT Pub. No.: WO96/18391

PCT Pub. Date: Jun. 20, 1996

[30] Foreign Application Priority Data

Dec. 14, 1994 [IT] Italy ................... MI9402512

[51] Int. Cl.⁶ ............ A61K 31/16; C07C 233/01; C07C 235/70; C07D 265/30
[52] U.S. Cl. ............ 514/613; 514/676; 514/679; 514/716; 544/107; 562/555; 564/152
[58] Field of Search .............. 514/613, 676, 514/679, 716; 562/555; 544/107; 564/152

[56] References Cited

FOREIGN PATENT DOCUMENTS

550008 A2  7/1993  European Pat. Off.

OTHER PUBLICATIONS

Munro et al., Nature, vol. 365 pp. 61–65, 1993.
Facci et al., Proc. Natl. Acad. Sci. USA vol. 92 pp. 3376–3380, 1995.

*Primary Examiner*—Johann Richter
*Assistant Examiner*—Taofiq A. Solola
*Attorney, Agent, or Firm*—Watov & Kipnes, P.C.

[57] ABSTRACT

The following description concerns a therapeutic method for the treatment of diseases connected with the modulation of the cannabinoid peripheral receptor, comprising administering amidic derivatives of mono and bicarboxylic acids with aminoalcohols or arninoethers selectively active on said receptor.

18 Claims, 2 Drawing Sheets

THERAPEUTIC USE OF MONO AND BICARBOXYLIC ACID AMIDES ACTIVE AT THE PERIPHERAL CANNABINOID RECEPTOR

This application is a 371 of PCT/EP95/04927, filed Dec. 13, 1995.

FIELD OF THE INVENTION

The present invention relates to a therapeutic method for the treatment of diseases connected with the modulation of the cannabinoid peripheral receptor, comprising administering amidic derivatives of mono and bicarboxylic acids with substituted aminoalcohols or aminoethers.

PRIOR ART DISCLOSURE

Cannabinoids are a specific class of psychoactive compounds present in Indian cannabis (Cannabis sativa), including about 60 different molecules, the most representative being cannabinol, cannabidiol and several isomers of tetrahydrocannabinol. Knowledge of the therapeutic activity of cannabis dates back to the ancient dynasties in China, where, already 5,000 years ago, cannabis was used for the treatment of asthma, migraine and some gynaecologic disorders. Said use later bacame so established that about in 1850 cannabis extracts were included in the US Pharmacopaeia and remained therein until 1947.

Cannabinoids are able to cause different effects at the level of various systems and/or organs; the most important effects occur on the central nervous system and on the cardiovascular system. In fact, they are able to affect mood, memory, motor coordination and cognition, and they increase heart rate and variate the systemic arterial pressure. Furthermore, it is well known the capability of cannabinoids to reduce intraocular pressure and to affect the respiratory and endocrine systems (L. E. Hollister, Health Aspects of Cannabis, Pharmacological Reviews, 38, 1–20, 1986). More recently, it was found that they suppress the cellular and humoral immune response and have antiinflammatory properties (A. W. Wirth et al., Antiinflammatory Properties of Cannabichromene, Life Science, 26, 1991–1995, 1980). However, the therapeutic use of cannabis is controversial both due to its relevant psychoactive effects, causing dependence and addiction, and to the manifold side effects that have not yet been completely clarified (L. E. Hollister, 1986, reference cited).

Notwithstanding the well established use of cannabis over the centuries, the mechanism of the effects of cannabinoids has been unknown until very recently. It was only in 1990 that Matsuda and collaborators identified and cloned a cannabinoid receptor belonging to the G-protein-coupled family of receptors; CB1 is coupled to G1 to inhibit adenilate cyclase activity and to a partussis-sensitive G protein to regulate $Ca^{2+}$ currents. Said receptor was found to be mainly located in the brain, in neural cell lines and only to a lesser extent at a peripheral level; therefore, in view of its localization, it was called Central Receptor (CB1) (Matsuda et al., Structure of a cannabinoid receptor and functional expression of the cloned cDNA, Nature, 346: 561–564, 1990). The discovery of a receptor led to assume the existence of a specific endogenous ligand.

In fact, subsequent research led to the isolation from pig brain of a substance able to exert an agonist action, i.e. capable of binding to the cannabinoid central receptor in a competitive way. Said substance was identified by structural investigation and by comparison with the synthetic product and was found to be an amidic derivative of arachidonic acid, and more particularly arachidonylethanolamide, later called anandamide. The pharmacological characterization of said molecule provided evidence that anandamide possesses a profile of activity which is similar to, though less potent than, Δ9-THC (tetrahydrocannabinol with a double bond in position 9), and is capable of mimicking the psychoactive effects thereof. Said evidences led to the conclusion that anandamide is the endogenous ligand of the cannabinoid central receptor (C. C. Felder et al., Anandamide, an Endogenous Cannabimimetic Eicosanoid, Binds to the Cloned Human Cannabinoid Receptor and Stimulates Receptor-mediated Signal Tranisduction, FNAS, 90, 7656–7660, 1993; P. B. Smich et al., The Pharmacological Activity of Anandamide, a Putative Endogenous Cannabinoid, in Mice, J. PET, 270, 219–227, 1994).

Subsequent researches brought about the individuation of substances binding to CB1 receptor; said substances, which may be grouped into a class of amidic compounds, were denominated anadamides by the authors (L. Hanus et al., Two New Unsaturated Fatty Acids Ethanolamides in the Brain that Bind to the Cannabinoid Receptor, J. Med.Chem., 36, 3032–3034, 1993). The discovery that the ethanolamide of arachidonic acid but not the ethanolamide of another biologically significant acid and anyway endogenously present in the brain such as palmitic acid, can functionally activate CB1 central receptor, brought about the subsequent identification of other amides of ethanolamine with highly unsaturated fatty acids, which have an affinity to CB1 receptor.

The multiplicity of effects of cannabinoids and CB1 receptor peculiar distribution led to assume the existence of differentiated receptor sites. In fact, a second different receptor for cannabinoids, called Peripheral Receptor (CX5 or CB2), was cloned. Being present in the spleen and macrophages/monocytes but absent at a central level, said receptor was regarded as responsible for mediating the cannabinoid-induced non-psychoactive effects (S. Munro et al., Molecular characterization of a peripheral receptor for cannabinoids, Nature, 365, 61–65, 1993). In this regard, the Δ9-THC ability to induce immunosuppressive effects was proved. Recent experimental results showed that Δ9-THC can cause alteration in the macrophagic function. In fact, the exposure to Δ9-THC decreases the cytolytic activity of activated macrophages, measured as TNF-α synthesis, release and cytotoxicity. Moreover, since macrophages release several cytolytic molecules, other than TNF-α, they were supposed to be a target for Δ9-THC (k. Fischer-Stenger et al., Δ9-Tetrahydrocannabinol Inhibition of Tumor Necrosis Factor-α: Suppression of Post-translational Events, J. PET, 267, 1558–1565, 1993). All the above evidences and the preferential massive localization of CB2 receptor at the immune system level prove that said receptor plays a specific role in mediating the immune and antiinflammatory response to stimuli of a different nature, the bacterial and viral ones included.

It was also demonstrated that anandamide, the endogenous ligand of CB1 central receptor, can bind to CB2 receptor with an affinity about 30 times lower than to the central receptor; this suggests the existence of another endogenous ligand for said receptor, so far unidentified (L. L. Iversen, Medical uses of marijuana?, Nature, 365, 12–13, 1993). As already mentioned, the therapeutic use of cannabinoids as analgesic, anti-emetic, anticonvulsant, spasmolytic and antiglaucoma agents, and, as more recently found, as anti-inflammatory agents, is inadvisable because of the cannabinoid-induced untoward side effects and psychoactive effects, as well as addiction and pharmacological dependence (W. L. Dewey, Cannabinoid Pharmacology, 38 (2), 151–178, 1986).

Some compounds, able to act as agonists indiscriminately on both cannabinoid receptors, have been recently developed: for example, it is known the use of dihydropyrrole-(1,2,3-d,e)-1,4-benzooxazine derivatives in the treatment of glaucoma (U.S. Pat. No. 5,112,820, Derwent abstract) and the use of diphenyl-pyrazole derivatives as immunomodulators or psychotropic agents in the treatment of various neuropathies, migraine, epilepsy, glaucoma etc. (European Patent Application EP 576 357, Derwent abstract). However said compounds, active on both CB1 central and CB2 peripheral receptors, may cause significant psychoactive effects, as well as addiction and habit.

In the light of the discovery that cannabinoids act through a receptorial mechanism and, in particular, on receptors able to mediate different functional effects, and that the two central and peripheral receptors, present little homology, it is evident the importance of developing a class of drugs acting selectively on the receptor subtype and not indiscriminately on both receptors, as is the case of natural and synthetic cannabinoids.

The investigations conducted to date on the pharmacological effects mediated by cannabinoid receptors show that the non-psychoactive effects of Cannabis derivatives are mediated by CB2 peripheral receptor. Furthermore, the CB2 receptor localization proves that said non-psychoactive effects, i.e. the effects on the immune system, the anti-inflammatory, myorelaxant and antinociceptive effects, as well as the effects on pressure systems, are mediated by said receptor.

The above evidences clearly show that it would be extremely important, from a therapeutic viewpoint, to obtain compounds capable of selectively acting on the cannabinoid peripheral receptor and, therefore, on the diseases connected with the modulation of said receptor, without causing psychoactive effects at a central level and the relevant side effects related to such action, such as habit and addiction.

The Applicant has recently found a class of N-acyl derivatives active on the modulation of mast cell degranulation processes, which act according to a local antagonist endogenous regulatior mechanism meant to control the mast cell degranulation induced by neurogenic and immunogenic supramaximal stimuli (ALIA=Autacoid Local Inflammation Antagonism). Said compounds can be advantageously used in the treatment of neurogenic and/or immunogenic autoimmune diseases, in particular multiple sclerosis and psoriasis, as disclosed in European Patent Applications EP 0 550 006 and EP 0 550 008. As known, the autoaggressive pathological phenomena of autoimmune diseases occur through local tissue injury, where specific immunocompetent cells, among which mast cells, play a central etiopathogenic role. In fact, mast cells are a cellular population diffused in the tissues which, becoming active in situ, causes biological inflammatory events with liberation of several highly cytotoxic chemical mediators, responsible for local tissue injury. Mast cell activity is controlled in an agonist sense by neuro and immunomediated activating systems, antagonized by inhibitory systems acting through general circuits, such as e.g. the corticosteroid hormones.

The Applicant found that a class of N-acyl-alkanolamides, in particular N-acyl-monoethanolamides and N-acyl-diethanolamides, is able to act on mast cells as a local antagonist system according to a mechanism of autacoid type; therefore, such compounds can be conveniently used in the treatment of diseases connected with acute or chronic inflammatory events, such as for example autoimmune diseases. To said class of compounds belongs also N-(2-hydroxyethyl)-hexadecanamide, or N-palmitoyl-ethanolamide (N-PEA), a compound whose activity was discovered accidentally in the '50s, following the identification of a generic cytoprotective activity of a lipidic excipient of an antirheumatic drug, which contained said compound. The pharmacological profile of such compound was later studied in experimental models of injury caused by various agents: the ability to increase the animal resistance to various bacterial toxins led to the subsequent pharmaceutical development of said compound. In fact, a pharmaceutical product was developed in Czechoslovakia in the form of tablets, suitable for preventing infections of the respiratory tract. Therefore, the Applicant found that the activity exerted by N-PEA and by the wide class of N-acyl derivatives described in the aforementioned patent applications does not limit to a generic and modest cytoprotective activity, but said class of compounds plays a specific and important role in local inhibitory modulation of mast cell degranulation.

Such an activity allows the use of the compounds belonging to said class as drugs, exerting not only a generic cytoprotective action, but specifically a modulation of mast cell degranulation and, therefore, an inhibitory action on the autoaggressive effects in autoimmune diseases and on the cytotoxic and lesive effects of diseases of different etiology, connected with inflammations. Said compounds are, therefore, capable of inhibiting the uncontrolled release of preformed mast cell granules, containing several proinflammatory mediators and, in particular, preformed granules containing Tumour Necrosis Factor (TNF-α), a highly cytotoxic cytokine involved in the autoaggressive autoimmunity process (R. Toms et al., J. Neuroimmunology, 30, 169–177, 1990; P. G. Kruger et al. Acta Neurol.Scand., 81, 331–336, 1990), as well as in lesive processes at the level of different tissues and organs.

Furthermore, the international application WO 95/25509, in the name of the same Applicant, discloses the use of N-acyl derivatives of aminoalcohols with mono and bicarboxylic acids in the therapeutic prevention and treatment of diseases associated with supramaximal and prolonged stimulation of the receptors of excitatory aminoacids (EAA), in particular of the N-methyl-D-aspartate (NMDA) receptor.

SUMMARY OF THE INVENTION

The Applicant has found that amides of mono and bicarboxylic aliphatic acids with aminoalcohols and aminoethers are able to bind selectively to cannabinoid peripheral receptor CB2 and to activate functionally the same.

Said amides have formula (I):

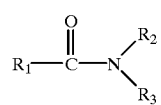

where $R_2$ and $R_3$ may belong to one of the following classes:
A) $R_2$ is the residue of a linear or branched hydroxyalkyl containing 1 to 20 carbon atoms, optionally substituted with one or more phenyl groups;
$R_3$ is H, $CH_3$ or $=R_2$;
B) $R_2$ is the residue of an alkylene-hydroxyphenyl, the aromatic ring being optionally substituted with one or more —OH and/or —OCH$_3$ groups, and the linear or branched alkylene chain containing 1 to 20 carbon atoms;

R$_3$ is H, CH or=R$_2$;

C) R$_2$ and R$_3$, with the nitrogen atom to which said two substituents are bound, form the residue of a cyclic aminoether containing 5 to 7 carbon atoms, optionally substituted with linear or branched alkyl groups.

In the aforesaid classes, the alcoholic function —OH can be optionally functionalized to give —OX, where X can be an alkyl, an acyl, an O-phosphate, the amiacyl of a bicarboxylic acid, an alkyl-sulphonate, a sulphate, a dialkylaminoacyl or an aminoacyl, X being optionally satisfied with monovalent or bivalent inorganic ions.

The substituent R$_1$ can be:

1) a linear or branched hydrocarbon radical containing 9 to 23 carbon atoms, preferably 11 to 17, either saturated or containing one double bond, optionally substituted with one or more —OH groups;

2) a group of formula (II):

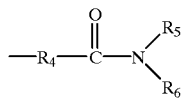

(II)

where R$_4$ is a linear or branched hydrocarbon radical containing 8 to 22 carbon atoms, preferably 10 to 16, either saturated or containing a double bond, optionally substituted with one or more —OH groups;

R$_5$ and R$_6$ are defined as R$_2$ and R$_3$ respectively.

Therefore, the object of the present invention is a therapeutic method for the treatment of diseases of mammals connected with the modulation of cannabinoid peripheral receptor, comprising administering an effective amount of at least one of said derivatives and of more soluble and/or slow-releasing derivatives thereof.

DETAILED DESCRIPTION OF THE INVENTION

Figure 1:
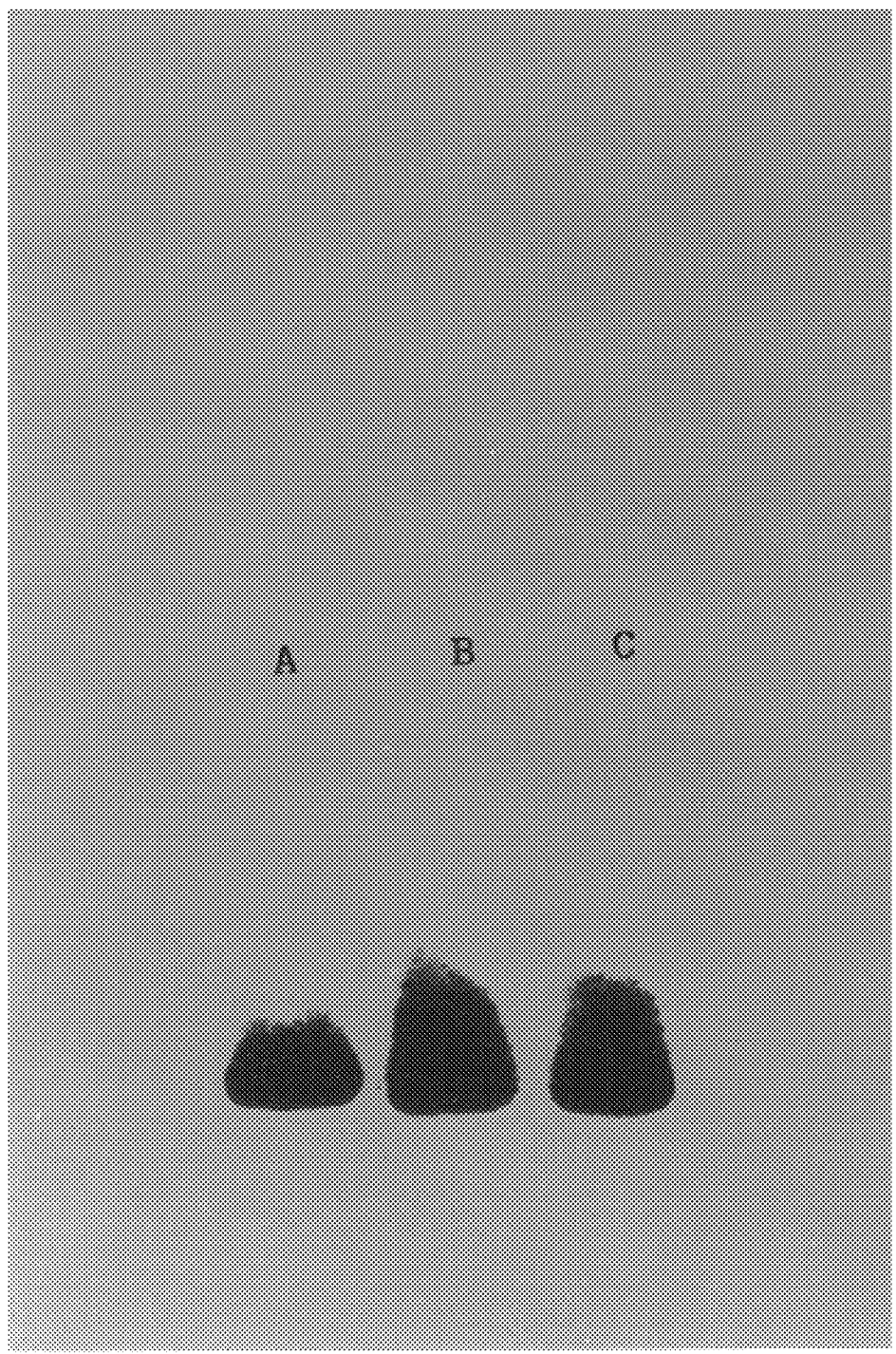
FIG. 1 illustrates the specific hybridization of cannabinoid peripheral receptor amplified by Polymerase Chain Reaction (PCR) in A) rat spleen, B) rat peritoneal mast cell cultures and C) RBL-2H3 cell cultures.

The characteristics and advantages of the mono and bicarboxylic acids amides with aminoalcohols or aminoethers, selectively active on the cannabinoid peripheral receptor and suitable for the treatment of diseases connected with the modulation of said receptor, according to the present invention, will be described in details hereinafter.

The Applicant has surprisingly found that the activity of N-PEA and of the amides of the invention does not limit to a generic cytoprotective action or to an inhibitory action on mast cell degranulation or to a protective effect against excitatory amino acids cytotoxicity in neural cells, as known in the prior art, but said compounds play an important and specific role in the selective activation of cannabinoid peripheral receptor.

The mono and bicarboxylic acids amides with aminoalcohols or aminoethers, active in the treatment of diseases connected with the modulation of cannabinoid peripheral receptor (CB2) or profiting by the activation of said receptor with a consequent negative modulation of cytotoxic and proinflammatory phenomena, according to the present invention, are defined by formula (I):

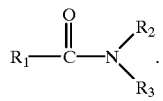

(I)

When R$_2$ and R$_3$ belong to class (A), R$_2$ preferably forms, with the nitrogen atom to which it is linked, the residue of monoethanolamine, diethanolamine, 2-hydroxypropylamine or di-(2-hydroxy-propyl)-amine; in these two last cases, the corresponding compound (I) may be optically active or racemic.

When alcoholic residues R$_2$ and R$_3$ belong to class (B), R$_2$ preferably forms, with the nitrogen atom to which it is linked, the residue of tyramine or 4-hydroxy-3-methoxybenzylamine, both optically active and racemic.

When alcoholic residues R$_2$ and/or R$_3$ belong to class (C), R$_2$ and R$_3$ preferably form, with the nitrogen atom to which they are linked, morpholine residue.

The hydroxyl groups —OH can be optionally functionalized in order to give —OX, where X can be an alkyl, preferably methyl or ethyl; an acyl, preferably —CO—CH3 or —C—Ph; an O-phosphate, preferably —PO$_3$H$_2$ or —PO$_2$H—O—CH$_2$—CH(OH)—CH$_2$—OH; the amiacyl of a bicarboxylic acid, preferably —CH$_2$—CH$_2$—COOH or —CO—(CH$_2$)$_3$—COOH, an alkyl-sulphonate, preferably —SO$_2$—CH$_3$, —SO$_2$—C$_6$H$_5$ or —SO$_2$—C$_6$H$_4$—CH$_3$; a sulphate; a dialkylaminoacyl, preferably —CO—CH$_2$—N (CH$_3$)$_2$; an aminoacyl, preferably —CO—CH(W)—NH$_2$, wherein W is the lateral chain of a natural aminoacid; X being optionally salified with monovalent or bivalent inorganic ions, and preferably K, Na, Mg or Ca.

The function of the group X is to increase the solubility in water and/or modify the pharmacokinetic properties of the compound, giving pro-drugs. When R$_1$ belongs to class (1), it forms, with the adjacent carbonyl, the acyl of a monocarboxylic acid, and preferably of lauric, myristic, palmitic, stearic, palmitoleic and oleic acids, or the homologues thereof substituted with hydroxyl groups, such as e.g. ω-hydroxypalmitic acid.

When R$_1$ belongs to class (2), R$_4$ forms, with the two adjacent carbonyls, the acyl of a bicarboxylic acid, and preferably of traumatic acid.

The products of the present invention may be prepared according to various known procedures, and preferably by high-temperature melting of the alkanolamine salt with the carboxylic acid, with formation of the relevant alkanolamide, or by acylation to the nitrogen atom of alkanolamine with a suitable carboxylic acid activated derivative, or by activation of the carboxyl of the acid with alkylchloroformate followed by aminolysis with alkanolamine.

Some examples of preparation of the amides of mono and bicarboxylic acids according to the present invention are reported hereinbelow for illustrative but not limitative purposes.

EXAMPLE 1

Preparation of N-palmitoyl-[(R)-2-amino-2-phenylethanol]

(R)-2-amino-2-phenylethanol (1.37 g; 10 mmol) and triethylamine (1.13 g; 11 mmol) were solubilized in anhydrous tetrahydrofuran (50 ml) at 0° C. A solution of palmitoyl chloride (2.74 g; 10 mmol) in anhydrous tetrahydrofuran (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness. The crude residue was taken up with water (20 ml) and extracted twice with ethyl acetate (20 ml). The organic phases were washed twice with water (15 ml), combined, dehydrated with anhydrous sodium sulphate and evaporated under vacuum. The residue was crystallized from tert-butyl-methyl-ether (30 ml). The product was separated by filtration, washed twice with tert-butyl-methyl-ether (5 ml), and dried in high vacuo.

The reaction yield was 88% approx.

The physico-chemical properties of N-palmitoyl-[(R)-2-amino-2-phenylethanol] were as follows:

physical state white crystalline powder molecular formula $C_{24}H_{41}NO_2$ molecular weight 375.59 elemental analysis C=76.75%; H=11.00%; N=3.73%; O=8.52% solubility in organic solvents >10 mg/ml in DMSO; >10 mg/ml in ethanol solubility in water scarcely soluble melting point 93–95° C.

TLC eluent: toluene-chloroform-acetone, 40/25/35; Rf=0.54

EXAMPLE 2

Preparation of N-palmitoyl-[(S)-2-amino-2-phenylethanol]

(S)-2-amino-2-phenylethanol (1.37 g; 10 mmol) and tri-ethylamine (1.13 g; 11 mmol) were solubilized in anhydrous tetrahydrofuran (50 ml) at 0° C. A solution of palmitoyl chloride (2.74 g; 10 mmol) in anhydrous tetrahydrofuran (20 ml) was added dropwise, over a period of 30 min, under continuous stirring at 0°C. The resulting mixture was stirred at 0° C. for 1 hr and at room temperature for additional 5 hrs. The resulting suspension was evaporated to dryness. The crude residue was taken up with water (20 ml) and extracted twice with ethyl acetate (20 ml). The organic phases were washed twice with water (15 ml), combined, dehydrated with anhydrous sodium sulphate and evaporated under vacuum. The residue was crystallized from tert-butyl-methyl-ether (30 ml). The product was separated by filtration, washed twice with tert-butyl-methyl-ether (5 ml) and dried in high vacuo.

The reaction yield was 91% approx.

The physico-chemical properties of N-palmitoyl-[(S)-2-amino-2-phenylethanol] were as follows:

physical state white crystalline powder molecular formula $C_{24}H_{41}NO_2$ molecular weight 375.59 elemental analysis C=76.75%; H=11.00%; N=3.73%; O=8.52% solubility in organic solvents >10 mg/ml in DMSO; >10 mg/ml in ethanol solubility in water scarcely soluble melting point 92–94° C.

TLC eluent: toluene/chloroform/acetone, 40:25:35; Rf=0.54

EXAMPLE 3

Preparation of N-(2-hydroxy-2-phenylethyl)-palmitoylanide 2-amino-1-phenylethanol (1.37 g; 10 mmol) and triethy-lamine (1.13 g; 11 mmol) were solubilized in anhydrous tetrahydrofuran (50 ml) at 0° C. A solution of palmitoyl chloride (2.74 g; 10 mmol) in anhydrous tetrahydrofuran (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness. The crude residue was taken up with water (20 ml) and extracted twice with ethyl acetate (20 ml). The organic phases were washed twice with water (15 ml), combined, dehydrated with anhydrous sodium sulphate and evaporated under vacuum. The residue was crystallized from cold ethanol (30 ml). The product was separated by filtration, washed twice with cold ethanol (5 ml) and dried in high vacuo.

The reaction yield was 93% approx.

The physico-chemical properties of N-(2-hydroxy-2-phenylethyl)-palmitoylamide were as follows:

physical state white crystalline powder molecular formula $C_{24}H_{41}NO_2$ molecular weight 375.59 elemental analysis C=76.75%; H=11.00%; N=3.73%; O=8.52% solubility in organic solvents >10 mg/ml in DMSO; >10 mg/ml in ethanol solubility in water scarcely soluble melting point 86–88° C.

TLC eluent: toluene-chloroform-acetone, 40/25/35; Rf=0.70

EXAMPLE 4

Preparation of N-palmitoyl-[(1S,2S)-(+)-2-amino-1-phenyl-1,3-propanediol (1S,2S)-(+)-2-amino-1-phenyl-1,3-propanediol (1.67 g; 10 mmol) and triethylamine (1.13 g; 11 mmol) were solu-bilized in anhydrous dimethylformamide (50 ml) at 0° C. A solution of palmitoyl chloride (2.74 g; 10 mmol) in anhy-drous dimethylformamide (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness under vacuum. The crude residue was taken up with water (20 ml) and extracted twice with ethyl acetate (20 ml). The organic phases were washed twice with water (15 ml), combined, dehydrated with anhydrous sodium sulphate and evaporated under vacuum. The residue was crystallized from cold ethanol 95° (30 ml). The product was separated by filtration, washed twice with cold ethanol 95° (5 ml) and dried in high vacuo.

The reaction yield was 89% approx.

The physico-chemical properties of N-palmitoyl-[(1S,2S)-(+)-2-amino-1-phenyl-1,3-propanediol] were as fol-lows:

physical state white crystalline powder molecular formula $C_{25}H_{43}NO_3$ molecular weight 405.62 elemental analysis C=74.03%; H=10.68%; N=3.45%; O=11.83% solubility in organic solvents >10 mg/ml in DMSO; >10 mg/ml in ethanol solubility in water scarcely soluble melting point 81–83° C.

TLC eluent: toluene-ethanol-acetic acid, 65/30/5; Rf=0.72

EXAMPLE 5

Preparation of N-palmitoyl-[(1S,2R)-(+)-norephedrine]

(1S,2R)-(+)-norephedrine (1.51 g; 10 mmol) and triethylamine (1.13 g; 11 mmol) were solubilized in anhydrous chloroform (50 ml) at 0° C. A solution of palmitoyl chloride (2.74 g; 10 mmol) in anhydrous chloroform (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness under vacuum. The crude residue was taken up with water (20 ml) and extracted twice with ethyl acetate (20 ml). The organic phases were washed twice with HCl 1N (15 ml) and twice with water (15 ml), combined, dehydrated with anhydrous sodium sulphate and evaporated under vacuum. The residue was crystallized from cold acetonitrile (30 ml). The product was separated by filtration, washed twice with cold acetonitrile (5 ml) and dried in high vacuo.

The reaction yield was 93% approx.

The physico-chemical properties of N-palmitoyl-[(1S,2R)-(+)-norephedrine] were as follows:

physical state white crystalline powder molecular formula $C_{25}H_{43}NO_2$ molecular weight 389.62 elemental analysis C=77.07%; H=11.12%; N=3.59%; O=8.21% solubility in organic solvents >10 mg/ml in DMSO; >10 mg/ml in ethanol solubility in water scarcely soluble melting point 83–85° C.

TLC eluent: toluene-ethanol-acetic acid, 65/30/5; Rf=0.75

EXAMPLE 6

Preparation of N-lauroyl-[(1S,2R)-(+)-norephedrine]

(1S,2R)-(+)-norephedrine (1.51 g; 10 mmol) and triethylamine (1.13 g; 11 mmol) were solubilized in anhydrous chloroform (50 ml) at 0° C. A solution of lauroyl chloride (2.19 g; 10 mmol) in anhydrous chloroform (20 ml) was added dropwise, over a period of 30 min, under continuous stirring at 0° C. The resulting mixture was stirred at 0° C. for 1 hr and at room temperature for additional 5 hrs. The resulting suspension was washed twice with HCl 1N (20 ml) and twice with water (15 ml). The aqueous phases were extracted twice with chloroform (15 ml). The organic phases were combined, dehydrated with anhydrous sodium sulphate and evaporated under vacuum. The residue was crystallized from cold acetonitrile (30 ml). The product was separated by filtration, washed twice with cold acetonitrile (5 ml), and dried in high vacuo.

The reaction yield was 89% approx.

The physico-chemical properties of N-lauroyl-[(1S,2R)-(+)-norephedrine] were as follows:

physical state white crystalline powder molecular formula $C_{21}H_{35}NO_2$ molecular weight 333.51 elemental analysis C=75.63%; H=10.58%; N=4.20%; O=9.59% solubility in organic solvents >10 mg/ml in DMSO; >10 mg/ml in ethanol solubility in water scarcely soluble melting point 72–74° C.

TLC eluent: toluene-ethanol-acetic acid, 65/30/5; Rf=0.70

EXAMPLE 7

Preparation of N-palmitoyl-[(1R,2S)-(−)-norephedrine]

(1R,2S)-(−)-norephedrine (1.51 g; 10 mmol) and triethylamine (1.13 g; 11 mmol) were solubilized in anhydrous chloroform (50 ml) at 0° C. A solution of palmitoyl chloride (2.74 g; 10 mmol) in anhydrous chloroform (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness under vacuum. The crude residue was taken up with water (20 ml) and extracted twice with ethyl acetate (20 ml). The organic phases were washed twice with HCl 1N (15 ml) and twice with water (15 ml), combined, dehydrated with anhydrous sodium sulphate and evaporated under vacuum. The residue was crystallized from cold acetonitrile (30 ml). The product was separated by filtration, washed twice with cold acetonitrile (5 ml) and dried in high vacuo.

The reaction yield was 90% approx.

The physico-chemical properties of N-palmitoyl-[(1R,2S)-(−)-norephedrine] were as follows:

physical state white crystalline powder molecular formula $C_{25}H_{43}NO_2$ molecular weight 389.62 elemental analysis C=77.07%; H=11.12%; N=3.59%; O=8.21% solubility in organic solvents >10 mg/ml in DMSO; >10 mg/ml in ethanol solubility in water scarcely soluble melting point 82–84° C.

TLC eluent: toluene-ethanol-acetic acid, 65/30/5; Rf=0.56

EXAMPLE 8

Preparation of N-lauroyl-[(1R,2S)-(−)-norephedrine]

(1R,2S)-(−)-norephedrine (1.51 g; 10 mmol) and triethylamine (1.13 g; 11 mmol) were solubilized in anhydrous chloroform (50 ml) at 0° C. A solution of lauroyl chloride (2.19 g; 10 mmol) in anhydrous chloroform (20 ml) was added dropwise, over a period of 30 min, under continuous stirring at 0° C. The resulting mixture was stirred at 0° C. for 1 hr and at room temperature for additional 5 hrs. The resulting suspension was washed twice with HCl 1N (20 ml) and twice with water (15 ml) The aqueous phases were extracted twice with chloroform (15 ml). The organic phases were combined, dehydrated with anhydrous sodium sulphate and evaporated under vacuum. The residue was crystallized from cold acetonitrile (30 ml). The product was separated by filtration, washed twice with cold acetonitrile (5 ml) and dried in high vacuo.

The reaction yield was 89% approx.

The physico-chemical properties of N-lauroyl-[(1R,2S)-(−)-norephedrine] were as follows:

physical state white crystalline powder molecular formula $C_{21}H_{35}NO_2$ molecular weight 333.51 elemental analysis C=75.63%; H=10.58%; N=4.20%; O=9.59% solubility in organic solvents >10 mg/ml in DMSO; >10 mg/ml in ethanol solubility in water scarcely soluble melting point 72–74° C.

TLC eluent: toluene-ethanol-acetic acid, 65/30/5; Rf=0.70

EXAMPLE 9

Preparation of N-palmitoyl-[(S)-(−)-2-amino-3-phenyl-1-propanol]

(S)-(−)-2-amino-3-phenyl-1-propanol (1.51 g; 10 mmol) and triethylamine (1.13 g; 11 mmol) were solubilized in anhydrous tetrahydrofuran (50 ml) at 0° C. A solution of palmitoyl chloride (2.74 g; 10 mmol) in anhydrous tetrahydrofuran (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness under vacuum. The crude residue was taken up with water (20 ml) and extracted twice with ethyl acetate (20 ml). The organic phases were washed twice with HCl 1N (15 ml) and twice with water (15 ml), combined, dehydrated with anhydrous sodium sulphate and evaporated under vacuum. The residue was crystallized from cold ethanol (30 ml). The product was separated by filtration, washed twice with cold ethanol (5 ml) and dried in high vacuo.

The reaction yield was 94% approx.

The physico-chemical properties of N-palmitoyl-[(S)-(−)-2-amino-3-phenyl-1-propanol] were as follows:

physical state white crystalline powder molecular formula $C_{25}H_{43}NO_2$ molecular weight 389.62 elemental analysis C=77.07%; H=11.12%; N=3.59%; O=8.21% solubility in organic solvents >10 mg/ml in $CHCl_3$;

solubility in water scarcely soluble melting point 96–98° C.

TLC eluent: toluene-ethanol-acetic acid, 65/30/5; Rf=0.70

EXAMPLE 10

Preparation of N-palmitoyl-[(R)-(+)-2-amino-3-phenyl-1-propanol]

(R)-(+)-2-amino-3-phenyl-1-propanol (1.51 g; 10 mmol) and triethylamine (1.13 g; 11 mmol) were solubilized in anhydrous tetrahydrofuran (50 ml) at 0° C. A solution of palmitoyl chloride (2.74 g; 10 mmol; in anhydrous tetrahydiofuran (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness under vacuum. The crude residue was taken up with water (20 ml) and extracted twice with ethyl acetate (20 ml). The organic phases were washed twice with HCl 1N (15 ml) and twice with water (15 ml), combined, dehydrated with anhydrous sodium sulphate and evaporated under vacuum. The residue was crystallized from cold ethanol (30 ml). The product was separated by filtration, washed twice with cold ethanol (5 ml) and dried in high vacuo.

The reaction yield was 89% approx.

The physico-chemical properties of N-palmitoyl-[(R)-(+)-2-amino-3-phenyl-1-propanol] were as follows:

physical state white crystalline powder molecular formula $C_{25}H_{43}NO_2$ molecular weight 389.62 elemental analysis C=77.07%; H=11.12%; N=3.59%; O=8.21% solubility in organic solvents >10 mg/ml in $CHCl_3$;

solubility in water scarcely soluble melting point 96–98° C.

TLC eluent: toluene-ethanol-acetic acid, 65/30/5; Rf=0.70

EXAMPLE 11

Preparation of N-(p-hydroxyphenylethyl)-lauroylamide

Tyramine (1.37 g; 10 mmol) and triethylamine (1.13 g; 11 mmol) were solubilized in isopropanol (50 ml) at −5° C. A solution of lauroyl chlorine (2.19 g, 10 mmol) in anhydrous chloroform (20 ml) was added dropwise, over a period of 30 min, under continuous stirring at 0° C. The resulting mixture was evaporated to dryness and the residue was taken up with ethyl acetate (70 ml). The resulting solution was washed twice with HCl 1N (20 ml) and twice with water (15 ml). The aqueous phases were extracted twice with ethyl acetate (15 ml). The organic phases were combined, decolourized with bone charcoal, dehydrated with anhydrous sodium sulphate and evaporated under vacuum. The residue was crystallized from tert-butyl-methyl-ether (30 ml). The product was separated by filtration, washed twice with cold tert-butyl-methyl-ether (5 ml) and dried in high vacuo.

The reaction yield was 89% approx.

The physico-chemical properties of N-(p-hydroxyphenylethyl)-lauroylamide were as follows:

physical state white crystalline powder molecular formula $C_{20}H_{33}NO_2$ molecular weight 319.49 elemental analysis C=75.19%; H=10.41%; N=4.38%; O=10.02% solubility in organic solvents >10 mg/ml in DMSO; >10 mg/ml in ethanol solubility in water scarcely soluble melting point 93–95° C.

TLC eluent: toluene-ethanol-acetic acid, 65/30/5; Rf=0.68

EXAMPLE 12

Preparation of N-(3-hydroxypropyl)-lauroylamide 3-amino-1-propanol (0.75 g; 10 mmol) and triethylamine (1.13 g; 11 mmol) were solubilized in anhydrous ethyl acetate (50 ml) at 0° C. A solution of lauroyl chloride (2.19 g; 10 mmol) in anhydrous ethyl acetate (20 ml) was added dropwise, over a period of 30 min, under continuous stirring at 0° C. The resulting mixture was stirred at 0° C. for 1 hr and at room temperature for additional 5 hrs. The resulting suspension was extracted three times with water (20 ml) and the aqueous phases were extracted again twice with ethyl acetate (20 ml). The organic phases were combined, dehydrated with anhydrous sodium sulphate and concentrated to a volume of 20 ml approx. The solution was allowed to crystallize at 0° C. and the crystalline fraction was separated by filtration, washed twice with ethyl acetate (5 ml) and dried in high vacuo.

The reaction yield was 95% approx.

The physico-chemical properties of N-(3-hydroxypropyl)-lauroylamide were as follows:
physical state white crystalline powder
molecular formula $C_{15}H_{31}NO_2$
molecular weight 257.42
elemental analysis C=69.99%; H=12.14%; N=5.44%; O=12.43%
solubility in organic
solvents >10 mg/ml in DMSO; >10 mg/ml in ethanol
solubility in water scarcely soluble
melting point 77–79° C.
TLC eluent: toluene-ethanol-acetic acid, 65/30/5; Rf=0.52

EXAMPLE 13

Preparation of N,N'-bis-(3-hydroxypropyl)trans-2-dodecenediamide

Traumatic acid (2.28 g; 10 mmol) was solubilized in anhydrous dimethylformamide (40 ml) at 0° C. with pyridine (2 ml). N-hydroxysuccinimide (2.53 g; 22 mmol) and dicyclohexylcarbodiimide (4.12 g; 20 mmol) were added to the above solution and the resulting mixture was stirred at 0° C. for 2 hrs. The urea formed was separated by filtration and discarded. The solution containing the succinimide ester was stirred again at 0° C. and added with 3-amino-1-propanol (2.25 g; 30 mmol). The resulting mixture was stirred overnight at room temperature and evaporated to dryness under vacuum. The residue was crystallized twice from water (60 ml). The crystalline fraction was separated by filtration, washed twice with water (5 ml) and dried in high vacua.

The reaction yield was 92% approx.

The physico-chemical properties of N,N'-bis(3-hydroxypropyl)-trans-2-dodecenediamide were as follows:
physical state white crystalline powder
molecular formula $C_{18}H_{34}N_2O_4$
molecular weight 342.48
elemental analysis C=63.13%; H=10.01%; N=8.18%; O=18.69%
solubility in organic
solvents >5 mg/ml in DMSO;
solubility in water scarcely soluble
melting point 142–143° C.
TLC eluent: chloroform-methanol-water-$NH_3$ (28%), 80/25/2/1; Rf=0.59

EXAMPLE 14

Preparation of N-methyl-N-(2-hydroxyethyl)-palmitoylamide

A mixture of palmitic acid (2.57 g; 10 mmol) and 2-(methylamino)-ethanol (1.13 g; 15 mmol) was fed to a flask provided with reflux condenser and heated on an oil bath to 160° C. for 6 hrs. The mixture was cooled, solubilized in ethyl acetate (100 ml) and extracted twice with NaOH 0.1N (20 ml), twice with HCl 0.1N (20 ml) and twice with $H_2O$ (20 ml). The aqueous phases were washed twice with ethyl acetate (10 ml). The organic phases were combined, dehydrated with sodium sulphate and evaporated to dryness. The residue was purified by silica gel column chromatography eluting with chloroform-methanol, 85/15. The fractions containing the product were combined and evaporated to dryness. The residue was dried in high vacuo.

The reaction yield was 80% approx.

The physico-chemical properties of N-methyl-N-(2-hydroxyethyl)-palmitoylamide were as follows:
physical state white amorphous powder
molecular formula $C_{19}H_{39}NO_2$
molecular weight 313.52
elemental analysis C=72.79%; H=12.54%; N=4.47%; O=10.20%
solubility in organic
solvents >10 mg/ml in DMSO; >10 mg/ml in n-octanol
solubility in water scarcely soluble
melting point
TLC eluent: chloroform-methanol-water-$NH_3$ (28%), 80/25/2/1; Rf=0.80

EXAMPLE 15

Preparation of 2-(N-palmitoylamino)-1,3-propandiol 2-amino-1,3-propanediol (0.91 g; 10 mmol) and triethylamine (1.13 g; 11 mmol) were solubilized in anhydrous tetrahydrofuran (50 ml) at 0° C. A solution of palmitoyl chloride (2.74 g; 10 mmol) in anhydrous tetrahydrofuran (20 ml) was added dropwise, over a period of 30 min, under continuous stirring at 0° C. The resulting mixture was stirred at 0° C. for 1 hr and at room temperature for additional 5 hrs. The resulting suspension was evaporated to dryness. The crude residue was taken up with water (20 ml) and extracted twice with ethyl acetate (20 ml). The organic phases were washed twice with water (15 ml), combined, dehydrated with anhydrous sodium sulphate and evaporated under vacuum. The residue was crystallized from cold ethanol (30 ml); the product was separated by filtration, washed twice with ethanol (5 ml) and dried in high vacuo.

The reaction yield was 89% approx.

The physico-chemical properties of 2-(N-palmitoylamino)-1,3-propandiol were as follows:
physical state white crystalline powder
molecular formula $C_{29}H_{39}NO_3$
molecular weight 329.52
elemental analysis C=69.25%; H=11.93%; N=4.25%; O=14.57%
solubility in organic
solvents >5 mg/ml in DMSO; >5 mg/ml in ethanol
solubility in water scarcely soluble
melting point 124.5–126.5° C.
TLC eluent: toluene-ethanol-acetic acid, 65/30/5; Rf=0.48

EXAMPLE 16

Preparation of N-palmitoylethanolamine glycerophosphate

Glycerophosphorylethanolamine (2.15 g; 10 mmol) was suspended under continuous stirring at 0° C. in a mixture consisting of NaOH 0.5M (40 ml) and chloroform (20 ml). The mixture was added dropwise, over a period of 30 min, with palmitoyl chloride (2.75 g; 10 mmol). The resulting mixture was allowed to stir overnight at 0° C. and then acidified with HCl 6. The organic phase was separated. The aqueous phase was extracted twice with chloroform (10 ml) and discarded. The organic extracts were washed twice with water (10 ml), combined and evaporated to dryness. The crude product was purified by silica gel column chromatography, eluting with chloroform-methanol-water, 70/30/3.5. The fractions containing the pure product were combined, evaporated to dryness and the residue was dried in high vacuo.

The reaction yield was 86% approx.

The physico-chemical properties of N-palmitoylethanolamine glycerophosphate were as follows:

physical state white amorphous powder
molecular formula $C_{21}H_{44}NO_7P$
molecular weight 453.55
elemental analysis C=55.61%; H=9.78%; N=3.09%; O=24.69%; P=6.83%
solubility in organic
solvents >10 mg/ml in DMSO;
solubility in water scarcely soluble (>1 mg/ml in phosphate buffer 50mM, pH 7.4
melting point
TLC eluent: chloroform-methanol-water-$NH_3$ (28%), 50/40/7/3; Rf=0.85

EXAMPLE 17

Preparation of N,N'-bis(4-hydroxybutyl)-trans-2-dodecendiamide

Traumatic acid (2.28 g; 10 mmol) was solubilized in anhydrous dimethylformamide (40 ml) at 0° C. with pyridine (2 ml) and added with N-hydroxysuccinimide (2.53 g; 22 mmol) and dicyclohexyl-carbodiimide (4.12 g; 20 mmol). The resulting mixture was stirred at 0° C. for 2 hrs. The urea formed was separated by filtration and discarded. The solution containing succinimide ester was stirred again at 0° C. and added with 4-amino-1-butanol (2.67 g; 30 mmol). The resulting mixture was allowed to stir overnight at room temperature, then evaporated to dryness under vacuum. The residue was crystallized twice from water (60 ml). The crystalline fraction was separated by filtration, washed twice with water (5 ml) and finally dried in high vacuo.

The reaction yield was 92% approx.

The physico-chemical properties of N,N'-bis-(4-hydroxybutyl)-trans-2-dodecendiamide were as follows:

physical state white crystalline powder
molecular formula $C_{20}H_{38}N_2O_4$
molecular weight 370.53
elemental analysis C=64.83%; H=10.34%; N=7.56%; O=17.27%
solubility in organic
solvents >5 mg/ml in DMSO;
solubility in water scarcely soluble
melting point 150–152° C.
TLC eluent: chloroform-methanol-water-$NH_3$ (28%), 80/25/2/1; Rf=0.60

EXAMPLE 18

Preparation of N-(4-hydroxybutyl)-lauroylamide 4-amino-1-butanol (0.89 g; 10 mmol) and triethylamine (1.13 g; 11 mmol) were solubilized in ethyl acetate (50 ml) at −5° C. A solution of lauroyl chloride (2.19 g; 10 mmol) in anhydrous ethyl acetate (20 ml) was added dropwise, over a period of 30 min. under continuous stirring at 0° C. The resulting mixture was stirred at 0° C. overnight, washed twice with HCl 1N (20 ml) and twice with water (15 ml). The aqueous phases were extracted twice with ethyl acetate (15 ml). The organic phases were combined, dehydrated with anhydrous sodium sulphate and evaporated under vacuum. The residue was crystallized from tert-butyl-methyl-ether (30 ml); the product was separated by filtration, washed twice with cold tert-butyl-methyl-ether (5 ml) and dried in high vacuo.

The reaction yield was 92% approx.

The physico-chemical properties of N-(4-hydroxybutyl)-lauroylamide were as follows:

physical state white crystalline powder
molecular formula $C_{16}H_{33}NO_2$
molecular weight 271.45
elemental analysis C=70.80%; H=12.25%; N=5.16%; O=11.79%
solubility in organic
solvents >10 mg/ml in DMSO; >10 mg/ml in ethanol
solubility in water scarcely soluble
melting point 93–95° C.
TLC eluent: toluene-ethanol-acetic acid, 65/30/5; Rf=0.60

EXAMPLE 19

Preparation of N-(2-hydroxyethyl)-palmitoleylamide

A mixture of palmitoleic acid (2.54 g; 10 mmol) and triethylamine (1.06 g; 10.5 mmol) in anhydrous chloroform (100 ml), allowed to stir at −10° C. in a nitrogen environment, was added dropwise, over a period of 30 min, with a solution of isobutylchloroformate (1.44 g; 10.5 mmol) in anhydrous chloroform (50 ml). The resulting mixture was stirred at −10° C. for 1 hr and at 0° C. for an additional 1 hr. To the mixture was added dropwise ethanolamine (0.9 g) over a period of 10 min. After an additional 2-hr stirring at 0° C., the mixture was evaporated to dryness. The residue was purified by silica gel column chromatography, eluting with chloroform-methanol, 98/2 v/v. The eluate fractions containing the product were combined and evaporated to dryness. The residue was crystallized from acetonitrile (30 ml), separated by filtration and dried in high vacuo.

The reaction yield was 92% approx.

The physico-chemical properties of N-(2-hydroxyethyl)-palmitoleylamide were as follows:

physical state white crystalline powder
molecular formula $C_{18}H_{35}NO_2$
molecular weight 297.48
elemental analysis C=72.68%; H=11.86%; N=4.71%; O=1076%
solubility in organic
solvents >10 mg/ml in DMSO; >10 mg/ml in ethanol
solubility in water scarcely soluble
melting point 55–57° C.
TLC eluent: chloroform/methanol/water-$NH_3$ (28%), 80/25/2/1; Rf=0.79

EXAMPLE 20

Preparation of N-(4-hydroxy-3-methoxybenzyl)-oleoylamide

Oleic acid (2.83 g; 10 mmol) and triethylamine (1.13 g; 11 mmol) were solubilized in dimethylformamide (30 ml) at 0°

C. and added with isobutylchloroformate (1.44 g; 10.5 mmol). The resulting solution was stirred at 0° C. for 20 min, then added with 4-hydroxy-3-methoxybenzylamine hydrochloride (1.90 g; 10 mmol) and triethylamine (1.13 g; 11 mmol) and allowed to stir overnight at 0° C. The resulting mixture was added with water (90 ml) and extracted three times with ethyl acetate (40 ml). The organic phases were washed twice with HCl 1N (20 ml) and twice with water (15 ml), combined, decolourized with bone charcoal, dehydrated with anhydrous sodium sulphate and evaporated under vacuum. The residue was purified by silica gel column preparative chromatography, eluting with hexane-ethylacetate-acetic acid, 70/30/0.5. The eluate fractions containing the pure product were combined, evaporated to dryness and the residue was finally dried in high vacuo.

The reaction yield was 90% approx.

The physico-chemical properties of N-(4-hydroxy-3-methoxybenzyl)-oleoylamide were as follows:

physical state white amorphous powder molecular formula $C_{26}H_{43}NO_3$ molecular weight 417.64 elemental analysis C=74.78%; H=10.38%; N=3.35%; O=11.49% solubility in organic solvents >10 mg/ml in DMSO >10 mg/ml in ethanol solubility in water scarcely soluble melting point TLC eluent: toluene-ethanol-acetic acid, 65/30/5; Rf=0.66

EXAMPLE 21

Preparation of N-(4-hydroxy-3-methoxybenzyl)-palmitoylamide 4-hydroxy-3-methoxybenzylamide hydrochloride (1.90 g; 10 mmol) and triethylamine (2.26 g; 22 mmol) were solubilized in dimethylformamide (30 ml) at 0° C. A solution of palmitoyl chloride (2.75 g; 10 mmol) in dimethylformamide (15 ml) was added dropwise, over a period of 30 min, under continuous stirring. The resulting mixture was stirred at 0° C. overnight, then added with water (90 ml) and extracted three times with tert-butyl-methyl-ether (40 ml). The organic phases were washed twice with HCl 1N (20 ml) and twice with water (15 ml), then combined, decolourized with bone charcoal, dehydrated with anhydrous sodium sulphate and evaporated under vacuum. The residue was crystallized from tert-butyl-methyl-ether (30 ml). The product was separated by filtration, washed twice with cold tert-butylmethyl ether (5 ml) and finally dried in high vacuo.

The reaction yield was 89% approx.

The physico-chemical properties of N-(4-hydroxy-3-methoxybenzyl)-palmitoylamide were as follows:

physical state white crystalline powder molecular formula $C_{24}H_{41}NO_3$ molecular weight 391.60 elemental analysis C=73.61%; H=10.55%; N=3.58%; O=12.26% solubility in organic solvents >10 mg/ml in DMSO >10 mg/ml in ethanol solubility in water scarcely soluble melting point TLC eluent: toluene-ethanol-acetic acid, 65/30/5; Rf=0.65

EXAMPLE 22

Preparation of N-(2-hydroxyethyl)-lauroylanmide

A mixture of lauric acid (2.00 g; 10 mmol) and ethanolamine (0.916 g; 15 mmol) was fed to a flask provided with reflux condenser and heated on an oil bath to 160° C. for 6 hrs.

The reaction mixture was directly crystallized from ethanol 80% (50 ml). The crystalline reaction was separated by filtration, washed three times with cold ethanol 80% (10 ml) and finally dried in high vacuo.

The reaction yield was 90% approx.

The physico-chemical properties of N-(2-hydroxyethyl)-lauroylamide were as follows:

physical state white crystalline powder molecular formula $C_{14}H_{29}NO_2$ molecular weight 243.39 elemental analysis C=69.09%; H=12.01%; N=5.76%; O=13.15% solubility in organic solvents >10 mg/ml in DMSO >10 mg/ml in chloroform solubility in water scarcely soluble melting point 85–87° C.

TLC eluent: chloroform-methanol-water-$NH_3$ (28%), 80/25/2/1; Rf=0.83

EXAMPLE 23

Preparation of N-(2-hydroxyethyl)-stearoylamide

A mixture of stearic acid (2.85 g; 10 mmol) and ethanolamine (0.916 g; 15 mmol) was fed to a flask provided with reflux condenser and heated on an oil bath to 160° C. for 6 hrs.

The reaction mixture was directly crystallized from ethanol 95% (50 ml). The crystalline fraction was separated by filtration, washed three times with cold ethanol 95% (10 ml) and finally dried in high vacuo.

The reaction yield was 90% approx.

The physico-chemical properties of N-(2-hydroxyethyl)-stearoylamide were as follows:

physical state white crystalline powder molecular formula $C_{20}H_{41}NO_2$ molecular weight 327.55 elemental analysis C=73.34%; H=12.62%; N=4.28%; O=9.77% solubility in organic solvents >5 mg/ml in chloroform solubility in water scarcely soluble melting point 98–100° C.

TLC eluent: chloroform-methanol-water-$NH_3$ (28%), 80/25/2/1; Rf=0.87

EXAMPLE 24

Preparation of N-(3-hydroxypropyl)-palmitamide

A mixture of palmitic acid (2.75 g; 10 mmol) and propanolamine (1.13 g; 15 mmol) was fed to a flask provided with reflux condenser and heated on an oil bath to 160° C. for 6 hrs.

The reaction mixture was directly crystallized from ethanol 95% (50 ml). The crystalline fraction was separated by filtration, washed three times with cold ethanol 95% (10 ml) and finally dried in high vacuo.

The reaction yield was 80% approx.

The physico-chemical properties of N-(3-hydroxypropyl)-palmitamide were as follows:
physical state white crystalline powder
molecular formula $C_{19}H_{39}NO_2$
molecular weight 313.53
elemental analysis C=72.79%; H=12.54%; N=4.47%; O=10.21%
solubility in organic
solvents >3 mg/ml in DMSO >10 mg/ml in n-octanol
solubility in water scarcely soluble
melting point 91–93° C.
TLC eluent: chloroform-methanol, 95/5; Rf=0.40

EXAMPLE 25

Preparation of N-palmitoylethanolamide

According to the method described by E. T. Roe et al., (J. Am. Chem. Soc., 74, 3442–3443, 1952), the synthesis of N-palmitoylethanolamide was obtained by refluxing ethanolamine with palmitic acid. In particular, palmitic acid (1 mol) was caused to react with ethanolamine (1.5 mol) in ethyl ether for 5–6 hrs under nitrogen atmosphere.

The reaction product was extracted from the reaction mixture and crystallized from ethanol 95% at 0° C. The melting point of N-PEA found was 94–95° C.

The physico-chemical properties of N-palmitoylethanolamide were as follows:
physical state crystalline powder
molecular formula $C_{18}H_{37}NO_2$
molecular weight 299.48
elemental analysis C=72.19%; H=12.45%; N=4.68%; O=10.69%
solubility in organic
solvents in hot MetOH, CHCl3, DMSO
solubility in water insoluble
melting point 94–95° C.
TLC eluent: toluene-chloroform, 9/1; Rf=0.75

EXAMPLE 26

Preparation of N,N'-bis(2-hydroxyethyl)-trans-2-dodecenediamide

A mixture of traumatic acid (4.57 g; 20 mmol) and triethylamine (4.26 g; 42 mmol) in anhydrous THF (150 ml) allowed to stir at −10° C., was dropwide added, over a period of 30 min, with a solution of isobutylchloroformate (5.74 g; 42 mmol) in THF (50 ml). The mixture was stirred at −10° C. for 2 hrs and at 0° C. for additional 15 hrs and added dropwise, over a period of 30 min, with ethanolamine (3.5 g). After stirring for additional 6 hrs at 0° C., the resulting suspension was filtered. The filtrate was discarded and the solid was dried under vacuum. The crude product obtained was crystallized from water (100 ml). The crystalline fraction was separated by filtration, washed three times with water (20 ml) and finally dried in high vacuo.

The reaction yield was 78% approx.

The physico-chemical properties of N,N'-bis(2-hydroxyethyl)-trans-2-dodecendiamide were as follows:
physical state white crystalline powder
molecular formula $C_{16}H_{30}N_2O_4$
molecular weight 314.43
elemental analysis C=61.12%; H=9.62%; N=8.91%; O=20.35%
solubility in organic
solvents >10 mg/ml in DMSO >10 mg/ml in ethanol
solubility in water >10 mg/ml at 95° C.
melting point 134–136° C.
TLC eluent: chloroform-methanol-water-$NH_3$ (28%), 80/25/2/1; Rf=0.57

EXAMPLE 27

Preparation of N-palmitoylethanolamide phosphate

N-(2-hydroxyethyl)-palmitoylethanolamide (3.0 g: 1C mmol) was solubilized in anhydrous methanesulphonic acid (10 ml) under stirring at 0° C. and added with phosphoric anhydride (2.12 g; 15 mmol). The resulting mixture was stirred at 0° C. for 25 hrs. The reaction mixture was added with ether to complete product precipitation. The precipitate was separated by centrifugation, dried under vacuum, washed with cold water and dried again under vacuum. The crude product obtained was hot washed with tert-butyl-methyl-ether (50 ml) and then crystallized from isopropanol (50 ml). The crystalline fraction was separated by filtration, washed three times with cold isopropanol (10 ml) and finally dried in high vacuo.

The reaction yield was 83% approx.

The physico-chemical properties of N-palmitoylethanolamide phosphate were as follows:
physical state white crystalline powder
molecular formula $C_{18}H_{38}NO_5P$
molecular weight 379.48
elemental analysis c=56.97%; H=10.09%; N=3.69%; O=21.08%; P=8.16%
solubility in organic
solvents >10 mg/ml in DMSO
solubility in water scarcely soluble (>1 mg/ml in phosphate buffer (50 mM), pH 7.4, NaCl 0.9%
melting point
TLC eluent: chloroform-methanol-water-$NH_3$ (30%), 50/40/7/3; Rf=0.38

EXAMPLE 28

Preparation of N-(2-hydroxyethyl)-10-undecenoylamide

10-Undecenoic acid (1.84 g; 10 mmol) was solubilized in anhydrous methanol (30 ml) and added with anhydrous H+sulphonic resin DOWEX 50X8®. The mixture was stirred at 30° C. for 72 hrs. The resin was separated by filtration, the solution was evaporated to dryness and the residue was added with ethanolamine (0.916 g) and allowed to stir at 60° C. for 20 hrs. The reaction mixture was directly crystallized from methanol-water ⅔ (50 ml) and the crystalline fraction was separated by filtration, washed three times with cold water (10 ml) and finally dried in high vacuo.

The reaction yield was 70% approx.

The physico-chemical properties of N-(2-hydroxyethyl)-10-undecenoylamide were as follows:
physical state white crystalline powder molecular formula $C_{13}H_{25}NO_2$ molecular weight 227.35 elemental analysis C=68.68%; H=11.08%; N=6.16%; O=14.07% solubility in organic solvents >10 mg/ml in DMSO >10 mg/ml in ethanol solubility in water scarcely soluble melting point 68.5–70.5° C.

TLC eluent: chloroform-methanol-water-$NH_3$ (28%), 88/25/2/1; Rf=0.57

EXAMPLE 29

Preparation of N-palmitoyl-morpholine

Morpholine (0.87 g; 10 mmol) and triethylamine (1.13 g; 11 mmol) were solubilized in anhydrous dimethylformamide (50 ml) at 0° C. A solution of palmitoylchloride (2.74 g; 10 mmol) was added dropwise, over a period of 30 min, under continuous stirring at 0° C. The resulting mixture was stirred at 0° C. for 1 hr and at room temperature for additional 5 hrs. The resulting suspension was evaporated to dryness under vacuum. The crude residue was washed in suspension with water, crystallized from cold ethanol 70% (30 ml). The product was separated by filtration, washed twice with cold ethanol 70% (5 ml) and dried in high vacuo.

The reaction yield was 92% approx.

The physico-chemical properties of N-palmitoylmorpholine were as follows:

physical state white crystalline powder molecular formula $C_{20}H_{39}NO_2$ molecular weight 325–53 elemental analysis C=73.79%; H=12.08%; N=4.30%; O=9.83% solubility in organic solvents >10 mg/ml in DMSO >10 mg/ml in hot ethanol solubility in water scarcely soluble melting point 45–46° C.

TLC eluent: chloroform-methanol, 95/5; Rf=0.94

EXAMPLE 30

Preparation of N-palmitoyl-[R(−)-2-amino-1-propanol]

R(−)-2-amino-1-propanol (0.75 g; 10 mmol) and triethylamine (1.1 g; 11 mmol) were solubilized in anhydrous tetrahydrofuran (30 ml) at 0° C. A solution of palmitoyl chloride (2.75 g; 10 mmol) in anhydrous tetrahydrofuran (15 ml) was slowly added over a period of 30 min, under continuous stirring at 0° C. The resulting mixture was kept under stirring overnight at 0° C., added with water (90 ml) and extracted three times with ethyle acetate (40 ml). The organic phases were washed twice with HCl 1N (20 ml) and twice with water (15 ml) combined, dehydrated with anhydrous sodium sulphate and evaporated under vacuum. The residue was crystallized from methanol (30 ml). The product was separated by filtration, washed twice with cold methanol (5 ml) and dried in high vacuo.

The reaction yield was 89% approx.

The physico-chemical properties of N-palmitoyl-[R(−)-2-amino-1-propanol] were as follows:

physical state white crystalline powder molecular formula $C_{19}H_{39}NO_2$ molecular weight 313.52 elemental analysis C=72.79%; H=12.54%; N=4.47%; O=10.21% solubility in organic solvents >10 mg/ml in ethanol; >5 mg/ml in DMSO;

solubility in water scarcely soluble melting point 87–89° C.

TLC eluent: toluene-ethanol-acetic acid, 65/30/5; Rf=0.63

EXAMPLE 31

Preparation of N-palmitoyl-[S(+)-2-amino-1-propanol]

S(+)-2-amino-1-propanol (0.75 g; 10 mmol) and triethylamine (1.1 g; 11 mmol) were solubilized in chloroform (30 ml) at 0° C. A solution of palmitoyl chloride (2.75 g; 1.0 mmol) in chloroform (15 ml) was slowly added dropwise over a period of 30 min, under continuous stirring at 0° C. The resulting mixture was kept under stirring overnight at 0° C. and added with water (60 ml); the organic phases were separated and the aqueous phases were extracted twice with chloroform (25 ml). The organic phases were washed twice with HCl 1N (20 ml) and twice with water (15 ml), combined, dehydrated with anhydrous sodium sulphate and evaporated under vacuum. The residue was crystallized from methanol (30 ml). The product was separated by filtration, washed twice with cold methanol (5 ml) and dried in high vacuo.

The reaction yield was 93% approx.

The physico-chemical properties of N-palmitoyl-[S(+)-2-amino-1-propanol] were as follows:

physical state white crystalline powder molecular formula $C_{19}H_{39}NO_2$ molecular weight 313.52 elemental analysis C=72.79%; H=12.54%; N=4.47%; O=10.21% solubility in organic solvents >10 mg/ml in ethanol; >5 mg/ml in DMSO;

solubility in water scarcely soluble melting point 87–89° C.

TLC eluent: toluene-ethanol-acetic acid, 65/30/5; Rf=0.63

EXAMPLE 32

Preparation of N-palmitoyl-[R(−)-1-amino-2-propanol]

R(−)-1-amino-2-propanol (0.75 g; 10 mmol) and triethylamine (1.1 g; 11 mmol) were solubilized in anhydrous tetrahydrofuran (30 ml) at 0° C. A solution of palmitoyl chloride (2.75 g; 10 mmol) ir anhydrous tetrahydrofuran (15 ml) was slowly added dropwise over a period of 30 min, under continuous stirring at 0° C. The resulting mixture was kept under stirring overnight at 0° C., added with water (90 ml) and extracted three times with ethyle acetate (40 ml). The organic phases were washed twice with HCl 1N (20 ml) and twice with water (15 ml), combined, dehydrated with anhydrous sodium sulphate and evaporated under vacuum. The residue was crystallized from methanol (30 ml). The product was separated by filtration, washed twice with cold methanol (5 ml) and dried in high vacuo.

The reaction yield was 92% approx.

The physico-chemical properties of N-palmitoyl-[R(−)-1-amino-2-propanol] were as follows:
  physical state white crystalline powder
  molecular formula $C_{19}H_{39}NO_2$
  molecular weight 313.52
  elemental analysis C=72.79%; H=12.54%; N=4.47%; O=10.21%
  solubility in organic
  solvents >5 mg/ml in ethanol;
  solubility in water scarcely soluble
  melting point 88–90° C.
  TLC eluent: toluene-ethanol-acetic acid, 65/30/5; Rf=0.63

EXAMPLE 33

Preparation of N-palmitoyl-[S(+)-1-amino-2-propanol]

S(+)-1-amino-2-propanol (0.75 g; 10 mmol) and triethylamine (1.1 g; 11 mmol) were solubilized in chloroform (30 ml) at 0° C. A solution of palmitoyl chloride (2.75 g; 10 mmol) in chloroform (15 ml) was slowly added dropwise over a period of 30 min, under continuous stirring at 0° C. The resulting mixture was kept under stirring overnight at 0° C. and added with water (60 ml); the organic phases were separated and the aqueous phases were extracted twice with chloroform (25 ml). The organic phases were washed twice with HCl 1N (20 ml) and twice with water (15 ml), combined, dehydrated with anhydrous sodium sulphate and evaporated under vacuum. The residue was crystallized from methanol (30 ml). The product was separated by filtration, washed twice with cold methanol (5 ml) and dried in high vacuo.

The reaction yield was 88% approx.

The physico-chemical properties of N-palmitoyl-[S(+)-1-amino-2-propanol] were as follows:
  physical state white crystalline powder
  molecular formula $C_{19}H_{39}NO_2$
  molecular weight 313.52
  elemental analysis C=72.79%; H=12.54%; N=4.47%; O=10.21%
  solubility in organic
  solvents >5 mg/ml in ethanol
  solubility in water scarcely soluble
  melting point 87–89° C.
  TLC eluent: toluene-ethanol-acetic acid, 65/30/5; Rf=0.63

EXAMPLE 34

Preparation of N-(p-hydroxy-phenylethyl)-palmitoylamide 2-(4-hydroxy-phenyl)-ethylamine (1.37 g; 10 mmol) and triethylamine (1.13 g; 11 mmol) were solubilized in tetrahydrofuran (30 ml) at 0° C. A solution of palmitoyl chloride (2.75 g; 10 mmol) in tetrahydrofuran (15 ml) was added dropwise, over a period of 30 min under continuous stirring at 0° C. The resulting mixture was stirred overnight at 0° C., added with water (90 ml) and extracted three times with tert-butyl-methylether. The organic phases were washed twice with HCl 1N (20 ml) and twice with water (15 ml), combined, decolorated with animal carbon, dehydrated with anhydrous sodium sulphate and evaporated under vacuum. The residue was crystallized from tert-butyl-methylether (30 ml). The product was separated by filtration, washed twice with cold tert-butyl-methylether (5 ml) and dried in high vacuo.

The reaction yield was 88% approx.

The physico-chemical properties of N-(p-hydroxy-phenylethyl)-palmitoylamide were as follows:
  physical state white crystalline powder
  molecular formula $C_{24}H_{41}NO_2$
  molecular weight 375.60
  elemental analysis C=76.75%; H=11.00%; N=3.73%; O=8.52%
  solubility in organic
  solvents >10 mg/ml in DMSO; >10 mg/ml in ethanol;
  solubility in water scarcely soluble
  melting point 105–106° C.
  TLC eluent: toluene-ethanol-acetic acid, 65:30:5; Rf=0.64

EXAMPLE 35

Preparation of N-(2-methoxy-ethyl)-palmitoylamide 2-methoxy-ethylamine (0.9 g; 12 mmol) and triethylamine (1.52 g; 15 mmol) were solubilized in tetrahydrofuran (30 ml) at 0° C. A solution of palmitoyl chloride (2.75 g; 10 mmol) in tetrahydrofuran (15 ml) was added dropwise, over a period of 30 min, under continuous stirring at 0° C. The resulting mixture was stirred overnight at 0° C., added with water (90 ml) and extracted three times with ethyle acetate (40 ml). The organic phases were washed twice with HCl 1N (20 ml) and twice with water (15 ml), combined, dehydrated with anhydrous sodium sulphate and evaporated under vacuum. The residue was crystallized from tert-butyl-methylether (30 ml). The product was separated by filtration, washed twice with cold tert-butyl-methylether (5 ml) and dried in high vacuo.

The reaction yield was 93% approx.

The physico-chemical properties of N-(2-methoxy-ethyl)-palmitoylamide were as follows:
  physical state white crystalline powder
  molecular formula $C_{19}H_{39}NO_2$
  molecular weight 313.52
  elemental analysis C=72.79%; H=12.54%; N=4.47%; O=10.21%
  solubility in organic
  solvents >10 mg/ml in ethanol
  solubility in water scarcely soluble
  melting point 73–75° C.
  TLC eluent: toluene-ethanol-acetic acid, 65/30/5; Rf=0.65

EXAMPLE 36

Preparation of N-lauroyl-morpholine

Morpholine (0.87 g; 10 mmol) and triethylamine (1.13 g; 11 mmol) were solubilized in anhydrous tetrahydrofuran (50 ml) at 0° C. A solution of lauroyl chloride (2.19 g; 10 mmol) in anhydrous tetrahydrofuran (20 ml) was added dropwise, over a period of 30 min, under continuous stirring at 0° C. The resulting mixture was stirred at 0° C. for 1 hr and at room temperature for additional 5 hrs. The resulting suspension was added with water (90 ml) and extracted three times with tert-butyl-methylether (40 ml). The organic phases were washed twice with HCl 1N (20 ml) and twice with water (15 ml), combined, decolorized with animal charcoal, dehydrated with anhydrous sodium sulphate and evaporated under vacuum. The residue was purified by silica gel column chromatography eluting with a mixture of hexane/ethyle acetate/acetic acid, 80/20/0.5. The fractions containing the pure product were combined and evaporated to dryness. The residue was dried in high vacuo.

The reaction yield was 90% approx.

The physico-chemical properties of N-lauroyl-morpholine were as follows:

physical state deliquescent amorphous powder molecular formula $C_{16}H_{31}N_2$ molecular weight 269.43 elemental analysis C=71.33%; H=11.60%; N=5.20%; O=11.88% solubility in organic solvents >10 mg/ml in DMSO; >10 mg/ml in ethanol;

solubility in water scarcely soluble melting point 21° C.

TLC eluent: hexane-ethyl acetate-acetic acid, 75/24/1; Rf=0.25

EXAMPLE 37

Preparation of N-stearoyl-morpholine

Morpholine (0.87 g; 10 mmol) and triethylamine (1.13 g; 11 mmol) were solubilized in anhydrous dimethylformamide (50 ml) at 0° C. A solution of stearoyl chloride (3.02 g; 10 mmol) in anhydrous dimethylformamide (20 ml) was added dropwise, over a period of 30 min, under continuous stirring at 0° C. The resulting mixture was stirred at 0° C. for 1 hr and at room temperature for additional 20 hrs. The resulting suspension was evaporated to dryness under vacuo. The crude product was washed in suspension with water, crystallized first from cold ethanol (30 ml) and then from tert-butyl-methylether (30 ml). The product was separated by filtration, washed twice with cold tert-butyl-methylether (5 ml) and dried in high vacuo.

The reaction yield was 89% approx.

The physico-chemical properties of N-stearoyl-morpholine were as follows:

physical state white crystalline powder molecular formula $C_{22}H_{43}NO_2$ molecular weight 325.59 elemental analysis C=74.73%; H=12.26%; N=3.96%; O=9.05% solubility in organic solvents >10 mg/ml in hot ethanol solubility in water scarcely soluble melting point 60–61° C.

TLC eluent: toluene-ethanol-acetic acid, 65/30/5; Rf=0.67

EXAMPLE 38

Preparation of 1,10-bis-morpholinylcarbonyl-trans-1-decene

Traumatic acid (2.28 g; 10 mmol) was solubilized in anhydrous dimethylformamide (40 ml) at 0° C. with pyridine (2 ml). N-hydroxysuccinimide (2.53 g, 22 mmol) and dicyclohexylcarbodiimide (4.12 g, 20 mmol) were added and the resulting mixture was stirred at 0° C. for 2 hours. The urea so formed was separated by filtration and discarded, while the solution containing the succinimidic ester was further stirred at 0° C. and added with morpholine (2.61 g, 30 mmol). The resulting mixture was stirred overnight at 30° C. and evaporated to dryness under vacuum. The crude residue was taken up with water (40 ml) and extracted three times with ethyl acetate (40 ml). The organic phases were combined, dehydrated with anhydrous sodium sulphate and evaporated under vacuum. The residue was crystallized twice from tert-butyl-methylether (50 ml). The product was separated by filtration, washed twice with cold tert-butyl-methylether (5 ml) and dried in high vacuo.

The reaction yield was 89% approx.

The physico-chemical properties of 1,10-bis-morpholinylcarbonyl-trans-1 decene were as follows:

physical state white crystalline powder molecular formula $C_{20}H_{34}N_2O_4$ molecular weight 366.51 elemental analysis C=65.54%; H=9.35%; N=7.64%; O=17.46% solubility in organic solvents >10 mg/ml in DMSO; >10 mg/ml in ethanol;

solubility in water scarcely soluble melting point 85–87° C.

TLC eluent: toluene-ethanol-acetic acid, 65/30/5; Rf=0.55

EXAMPLE 39

Preparation of N-(4-hydroxy-3-methoxybenzyl)-stearoylamide 4-hydroxy-3-methoxybenzylamine hydrochloride (1.90 g, 10 mmol) and triethylamine (2.26 g; 22 mmol) were solubilized in dimethylformamide (30 ml) at 0° C. A solution of steroyl chloride (3.03 g; 10 mmol) in dimethylformamide (15 ml) was added dropwise, over a period of 30 min, under continuous stirring at 0° C. The resulting mixture was stirred overnight at 0° C.; then the mixture was added with water (90 ml) and extracted three times with tert-butyl-methylether (40 ml). The organic phases were washed twice with HCl 1N (20 ml) and twice with water (15 ml), combined, decolorized with animal charcoal, dehydrated with anhydrous sodium sulphate and evaporated under vacuum. The residue was crystallized from tert-butyl-methylether (30 ml). The product was separated by filtration, washed twice with cold tert-butyl-methylether (5 ml) and dried in high vacuo.

The reaction yield was 91% approx.

The physico-chemical properties of N-(4-hydroxy-3-methoxybenzyl)-stearoylamide were as follows:

physical state white crystalline powder molecular formula $C_{26}H_{45}NO_3$ molecular weight 419.65 elemental analysis C=74.42%; H=10.81%; N=3.34%; O=11.44% solubility in organic solvents >10 mg/ml in DMSO; >10 mg/ml in ethanol;

solubility in water scarcely soluble melting point 87–89° C.

TLC eluent: toluene-ethanol-acetic acid, 65/30/5; Rf=0.66

As already mentioned, the amides of mono and bicarboxylic acids with aminoalcohols and aminoethers according to the present invention, corresponding to formula (I) reported hereinabove, can selectively bind to CB2 peripheral receptor, acting as competitive agonists and displacing from said receptor the natural and synthetic cannabinoids already known. Furthermore, said amides are capable of functionally activating CB2 receptor, by mimicking the non-psychoactive biological effects of cannabinoids and acting with a potency higher than or comparable with the one of cannabinoids.

The Applicant has also surprisingly found that CB2 cannabinoid peripheral receptor is present on mast cell. Furthermore, the Applicant has unexpectedly found that CB2 cannabinoid peripheral receptor is functionally expressed also on non-immune cells or tissue; in particular, the Applicant has found that CB2 is functionally expressed in Nervous System on cerebellar granule cells, indicating that such receptor can modulate also non-immune cell functions. This extremely important aspect of the present invention will be illustrated in detail hereinbelow.

A) Identification of CB2 Receptor on Mast Cells and Non-Immune Cells.

In order to verify that CB2 cannabinoid peripheral receptor is present on mast cells and on non-immune cells (i.e. neurons), the presence of messenger RNA for said receptor was investigated in primary cultures of rat peritoneal mast cells, in a basophilic-mastocyte cell line from rat solid tumour (Rat Basophilic Leukemia, RBL-2H3) and in mouse cerebellar granule cell culture, in comparison with rat spleen homogenate tissues, where the presence of said receptor is acknowledged.

Both Polymerase Chain Reaction and in situ hybridisation technique were used.

i) Cannibinoid Peripheral Receptor Specific Hybridisation Amplified by Polimerase Chain Reaction (PCR).

Extraction of Total mRNA from Tissues and Cells

Total RNA was extracted from rat peritoneal mast cells, RBL-2H3 cells and rat spleen, according to the method described by Chumczynski and Sacchi (Anal. Biochem., 162, 156–159, 1987).

$5 \times 10^6$ mast cells, cells RBL-2H3, or 50 mg of spleen were separately homogenized in a 1.5 ml polypropylene tube EPPENDORF® (safe-lock type) with guanidinium isothiocyanate 5M (600 µl). Each tube was then supplied with sodium acetate 2M (60 µl), pH 5, and phenol (600 µl) saturated in buffer Tris-HCl 1M, pH 7.0. The samples were briefly stirred by vortex mixing (Heidolpn, type REAX2000®) and then added with chloroform-isoamyl alcohol (49:1 v/v) (120 µl). After agitation for 15 sec. by vortex mixing and incubation in ice for 15 min, the samples were centrifuged at 15,000×g at 4° C. for 15 min. 600 µl of the upper aqueous phase was withdrawn and placed in another tube, having care to avoid any contact with the interface of the organic lower phase, which was discarded. The aqueous phase was added with isopropanol (600 µl) and, after agitation, the samples were incubated at −20° C. for at least 60 min and centrifuged at 15,000×g at 4° C. for 5 min. The supernatant was discarded. The pellet was washed with ethanol 80% and then with absolute ethanol, concentrated to dryness and suspended again in water. (20 µl). 2 µl of the sample were used for the spectrophotometric determination of RNA concentration at the wave length of 260 nm and for the visualization with ethidium bromide on agarose gel at 1%.

Reverse Transcription and Amplification by Polymerase Chain Reaction (PCR) of CR2 Receptor 1 µg of total RNA withdrawn from each of the above samples was subjected to reverse transcription, as described by Leon at al. (PNAS, 91: 3739–3743, 1994), using the reverse transcriptase of murine moloney leukaemic virus and 50 pmol of a synthetic oligonucleotide SEQ ID NO:1 of sequence: 5'-TAGGTAGGAGATCAAGCG-3', complementary and antiparallel to the MRNA coding for cannabinoid peripheral receptor (Munro et al., Nature 365, 61–65, 1993), in a total volume of 20 µl After 1-hr reaction at 37° C., the volume of the transcription product was brought to 100 µl with water and one fourth of the final volume was subjected to amplification by means of PCR. Said operation was conducted in 500 µl thin-walled test tubes, filled up to a final volume of 100 µl with a solution having the following composition:

50 mM TRIS HCl, pH 8.3, at 25° C.:
75 mM KCl;
2.5 mM $MgCl_2$;
10 mM DTT (dithiothreitol);
0.2 mM dATP, dCTP, dGTP and dTTP;
50 pmol sense primer SEQ ID NO:2: (5'-TTTCACGGTGTGGACTCC-3');
50 pmol antisense primer SEQ ID NO:3: (5'-TAGGTAGGAGATCAAGCG-3');
0.551 Taq Pol (Taq polymerase) 2.5 U/µl (Polymerase Stoffel fragment, CETUS/PERKINS ELMER®);
3% formamide.

Primers were specific for cannabinoid peripheral receptor. PCR was carried out for 35 thermal cycles in apparatus mod. 9600 of Cetus/Perkin Elmer®, according to the following procedure:

| Temperature | Duration |
|---|---|
| 95° C. | 1 min |
| 54° C. | 1 min |
| 72° C. | 1 min |

Once the reaction had been completed, 30 µl of the reaction volume was electrophoresed on 1% agarose gel in order to visualize the amplification products, then transferred and immobilized on a nylon filter for inner-probe hybridization to the two PCR primers.

Specific Hybridization with Inner Oligonucleotide

The identity of the amplification product was determined by hybridization with a synthetic oligonucleotide SEQ ID NO:4, complementary to amplified sequences of cannabinoid peripheral receptor, labelled with radioactive tracers.

The sequence of SEQ ID NO:4 was as follows:
5'-GGTGACGAGAGCTTTGTAGGTAGGTGGGTAG-CACAGACATAGGTA-3'

Radioactive labelling was carried out at 37° C. for 1 hr, using 5 pmol inner oligonucleotide, as follows:
33 pmol ($\alpha^{32}$P)-dATP (New England Nuclear);
20 U Terminal Deoxynucleotide Transferase (US Biochemical);
100 mM sodium cacodylate (pH 7.2)
2 mM $CoCl_2$
0.2 mM 2-mercaptoethanol
in a final volume of 20 µl The labelled products were purified by chromatography on SEPHADEX G-50® column, and added to the hybridization solution containing the filter with the PCR-amplified products. Hybridization and washings were carried out under standard conditions, as described by Sambrook, Fritsch and Maniatis (Molecular Cloning. A Laboratory Manual, Cold Spring Harbor Laboratory Press, 1989).

The hybridized filter was exposed to a autoradiographic film for the detection of the amplified bands of the cannabinoid peripheral receptor messenger.

ii) mRNA—Peripheral Cannabinoid Receptor in Situ Hybridisation.

The brains of adult male mice (20–22 g) were frozen in 2-methyl-butane at −80° C., sectioned with a cryostat and the 12 mm coronal sections were thaw-mounted on poly-L-lysine coated slides. All sections were then fixed in 4% paraformaldehyde (PFA) and dehydrated in a graded series of ethanol, including a 5 min. incubation in chloroform and air dried. Mouse cerebellar granule cells (15 day in vitro-DIV) cultured on poly-L-lysine coated coverslips were fixed in 4% PFA, washed twice in PBS and permeabilized in 70% ethanol at 4° C. for 48 hrs, dehydrated in higher graded ethanol and air dried. To detect the CB2-specific mRNA, was chosen the synthetic oligonucleotide (45 mers) CB2 (SEQ ID NO:4: 5'-GGTGACGAGAGCTTTGTAGGTA-GGTGGGTAGCACAGACATAGGTA-3 according to Munro et al., 1993, cited reference). A random sequence was utilized for control sections. All oligonucleotides were tailed with $^{35}$S-dATP (NEN) using terminal deoxynucleotidyl-transferase (Pharmacia) to a specific activity of $10^9$ cpm/mg. All sections were hybridized in standard solutions (*) with 1.5 107 dpm/ml overnight at 42° C. in a humidified chamber. Sections were then washed once in 1×SSC/0.1%(**) SDS at 55° C. for 30 min., then twice in 1×SSC at 55° C. for 15 min., followed by 0.1×SSC at 25° C. for 30 min., rinsed in autoclaved water for 2 min., dehydrated in ethanol and air dried. The slides were subsequently dipped in photoemulsion (Ilford K.5 diluted 1:1 in water), exposed for 5 weeks at 4° C., developed (Ilford Phenisol), fixed (Ilford Hypam), and counterstained with cresyl violet.

Standard Solution Preparation (*) Hybridisation cocktail Formamide: 5 ml, 50%; SSC 20×: 2 ml, 4×; Denhardt's 50×: 0.2 ml; 1×Lauryl-sacarosyl 20%: 0.5 ml, 1%; Destran sulphate: 1 g, 10% ; 200 mM Phosphate buffer pH 7.0: 1 ml, 20 mM, water-DEPC q.s.t o 10 ml. Filtrate using 0.45 $\mu$m filter and store at −20° C.

(**) Sodium Citrate Solution SCS 20×. Sodium chloride 175.3 g and sodium citrate 88.2 g were dissolved in 800ml DEPC-water; NaOH 10 M was used to adjust the pH 7.2. Add DEPC-water q.s. to 1000 ml for autoclave procedure.

Figure 2:
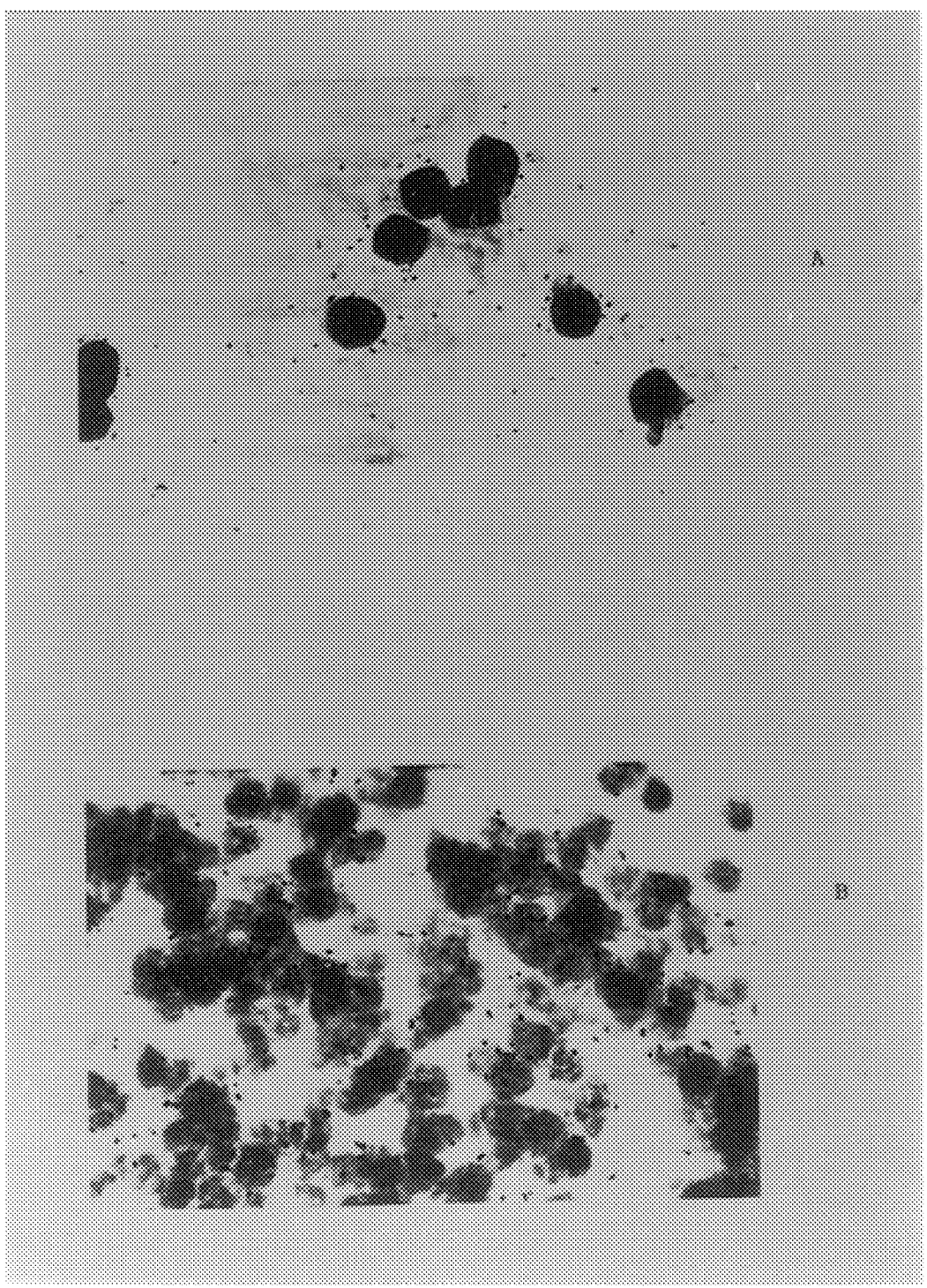
FIG. 2 illustrates the specific mRNA-CB2 cannabinoid peripheral receptor detected by in situ hybridisation in Cerebellar granule cells (FIG. 2A) and Cerebellum (FIG. 2B).

The autoradiographic examination shows that rat peritoneal mast cells and the cousin RBL-2H3 cells, cerebellar granule cells and cerebellum express, similarly to spleen preparations, mRNA specific to peripheral cannabinoid receptor CB2. This finding is clearly shown in FIGS. 1 and 2. FIG. 1 illustrates the specific hybridization of cannabinoid peripheral receptor amplified by Polymerase Chain Reaction (PCR) in (A) rat spleen, (B) rat peritoneal mast cell cultures and (C) RBL-2H3 cell cultures (C). FIG. 2 illustrates the specific mRNA-CB2 peripheral cannabinoid receptor in situ hybridisation.

B) Binding Assays

Specific binding assays were conducted for the purpose of checking whether the receptor was functionally expressed and whether the amides forming the object of the present invention were able to bind to CB2 receptor in a specific and competitive manner, compared with the cannabinoids having a known affinity to the receptor and compared with anandamide, the endogenous ligand of CB1 receptor.

a) Preparation of Plasmatic Membranes of RBL-2H3 Cells

RBL-2H3 cells ($100\times10^6$), frozen at −80° C., were thawed with 4 ml of Tris-HCl buffer solution 50 mM (pH 7.4), added with 0.25% w/v of Tripsin inhibitor, TYPE II-S: SOY BEAN® (distributed by Sigma). The cells were resuspended in the buffer and homogenized. The homogenate was centrifuged at 1500×g at 4° C. for 10 min. The supernatant obtained was collected and the precipitate was resuspended in 4 ml of the previous buffer. The resuspended precipitate was homogenized and centrifuged again at 1500×g at 4° C. for 5–10 min. The resulting supernatant was combined to the supernatant previously obtained and centrifuged at 5000×g for 10 min. After centrifugation, the supernatant was collected and further centrifuged at 40,000×g at 4° C. for 30 min. The resulting precipitate was resuspended in 0.5 ml of the buffer solution described above, with addition of 1% Bovine Serum Albumin fatty acid free. The obtained suspension was centrifuged at 40,000×g at 4° C. for 30 min. The resulting precipitate was collected and resuspended in buffer solution containing 50 mM Tris HCl, 1 mM Tris-EDTA, 3 mM $MgCl_2$, pH 7.4, in order to obtain a proteic concentration of 1 $\mu g/\mu l$ approx. This preparation may be used fresh, or frozen at −80° C. and utilized within few days.

b) "Binding" Assays Conditions to the Preparation of RBL-2H3 Cell Membranes

Saturation curve of labelled receptor agonist 3H-WIN 55,212-2 (specific activity 44 Ci/mmol, distributed by New England Nuclear): silanized plastic test tubes were fed, in the order, with binding buffer (50 mM Tris HCl, 1 mM Tris-EDTA, 3 mM $MgCl_2$, 0.5% w/v Bovine Serum Albumin fatty acid-free) to a final volume of 0.5 ml, decreasing doses of 3H-WIN 55,212-2 from 0.5 to 20 nM (final) and 30 $\mu$g membrane proteins prepared in item a). The resulting binding mixture was incubated at 30° C. for 60 min under stirring and centrifuged at 40,000×g at 20° C. for 15 min. After centrifugation, an aliquot portion of the supernatant was collected to calculate the concentration of the ligand not associated to the membranes. After removal of the supernatant residue, the precipitate was washed with 1 ml PBS (Phosphate Buffer Solution) containing 0.5% Bovine Serum Albumin, taken up with 50 $\mu l$ of a mixture of ethanol and 1% TRITON X-100 ® (50/50 v/v), incubated at 37° C. for 20 min and resuspended.

The resuspended material was added and mixed with scintillator liquid (3 ml) and placed in a "β-counter" for 5 min. To evaluate the "A specific Binding", the predetermined test tubes were fed first with unlabelled receptor agonist WIN 55,212-2 at a final concentration of 15 M and then with the labelled ligand. Said binding gives Kd=5–10 nM and Bmax =100–250 pM.

3H-WIN 55,212-2 Binding Displacement

For these competitions, 3H-WIN 55,212-2 was used at a concentration of 3 $\mu$M. Non-radioactive WIN 55,212-2 (1 $\mu$M) was used to inhibit specific binding. The competitors nabilone [3-(1,1-dimethylheptyl)-6,6a,7,8,10,10a-hexahydro-1-hydroxy-6,6-dimethyl-9H-dibenzo-[b,d]-pyran-9-one] and anandamide were solubilized in 0.1% ethanol, whereas the products forming the object of the present invention were solubilized in 0.1% DMSO. The competitors were added to the binding mixture prior to the labelled ligand. In both cases, for an evaluation of the reference specific binding, ethanol and DMSO were added at the same final concentration to the total binding and to the aspecific one, also in the absence of competitors.

The aforementioned binding assays provided evidence that the receptor expression was complete and functional.

The data of Tables 1 and 2 show that the amidic derivatives according to the present invention, like anandamide and the cannabinoid Nabilone, are able to bind to the receptor and to compete, with different potency, with the synthetic radioligand WIN 55,212-2.

Table 1

Competitive inhibition of |3H| WIN 55,212-2 specific binding by the compounds of the invention. |13H| WIN 55,212-2 was used at a concentration of 3 µM, whereas the other compounds were used at a concentration of 10 µM.

| Competitor | Specific binding | % Displacement |
|---|---|---|
| 0.1% DMSO* | 1433 | — |
| Example 1 | 325 | 77 |
| Example 19 | — | 100 |
| Example 22 | 400 | 72 |
| Example 25 | 1103 | 23 |
| Example 26 | 402 | 72 |
| Example 27 | 843 | 42 |
| Example 28 | 325 | 77 |
| 0.1% Ethanol** | 1843 | — |
| anandamide | 99 | 95 |
| Nabilone | — | 100 |

* 01.% DMSO is the concentration used for amides solubilization according to the present invention.
** 0.1% ethanol is the concentration used for anandamide and Nabilone solubilization.

Table 2

Competitive inhibition of [3H] WIN 55,212-2 binding to RBL-2H3 cell membranes by the amides of the invention and cannabinoids. Incubation was carried out in the presence of 1% DMSO. The values of Inhibitory Concentration 50 (IC50) are expressed as means ± SEM, after the number of experiments reported hereinbelow.

| Competitor | IC50 (nM) | no. of experiments |
|---|---|---|
| Nabilone | 2.6 ± 1.4 | 4 |
| Δ8-THC | 223 ± 120 | 6 |
| Cannabidiol | >1000 | 3 |
| Anandamide | 33 ± 29 | 5 |
| Example 1 | 0.4 | 1 |
| Example 22 | 18.08 | 2 |
| Example 25 | 1.0 ± 0.55 | 7 |
| Example 27 | 7.6 | 1 |

C) Biological Activity Assays

The biological activity deriving from CB2 receptor functional activation and, in particular, the ability of the amides of the invention to inhibit serotonin release, induced by specific stimulus, was evaluated on RBL cultures and compared with cannabinoids of known potency and with anandamide.

The specific binding and/or the functional effects of the amidic derivatives of the invention were evaluated.

For purpose of comparison, the following products were used: among natural cannabinoids, three different isomers of tetrahydrocannabinol (THC): Δ8-THC, Δ9-THC and 11-nor-Δ8-THC-9; among synthetic cannabinoids, Nabilone and WIN 55,212-2, in addition to the CB1 endogenous ligand, anandamide.

Preparation of RBL-2H3 Cell Cultures

RBL-2H3 cell cultures were grown in flasks (Falcon®), at 37° C., 5% $CO_2$, in the presence of Minimum Essential Eagle's Medium (MEM) and 4 mM glutamine, 100 U/ml penicillin and 20% deactivated fetal calf serum (DFCS).

RBL-2H3 Cell Sensitization and Activation

For each test. the cells were removed from the flasks with PBS, containing 0.5 mM EDTA at pH 7.2, and seeded in wells (96 well plate FALCON®) in the presence of RPMI-1640 medium (code 6504, distributed by Sigma) containing 50 mg/l gentamicin and 10% FCS at a density of 100,000 cells/100 µl medium/well. Furthermore, during seeding, said cells were loaded with serotonin by addition of 1 µCi/ml 3H-serotonin (5-hydroxy- triptamine 5HT, 26.4 Ci/mmol, New England Nuclear) and then incubated for 18 hrs (37° C., 5% $CO_2$). After 18-hr incubation in the presence of 3H-serotonin, the culture medium was removed and the cells were sensitized for 1 hr (37° C., 5% $CO_2$) in the presence of PIPES (N,N'-bis-(2- ethanesulphonyl)-piperazine, code 3768, Sigma)-buffered saline (100 µl/well), pH 7.1, containing 0.3 µg/ml mouse monoclonal antibody (IgE) against DNP (ADNP).

After removal of the sensitization medium, cells were activated—or not activated (control)—by addition, at 37° C. for 155 min, of PIPES (100 µl/well), pH 7.1, containing—or not containing (control)—0.1 µg/ml human albumin combined with dinitrophenyl (DNP-HSA) and containing a natural or synthetic cannabinoid or an amidic derivative according to the present invention. After incubation, the medium was collected and centrifuged to determine the 3H-serotonin quantity released from DNP-HSA-stimulated or not stimulated cells. In parallel, adhered cells were solubilized with 1% TRITON X-100 ® in PBS (100 µl/well) in order to determine the quantity of 3H-serotonin present in the cells. In both cases, the quantity of 3H-serotonin was measured by liquid scintillography and radioactivity counting, using a β-counter of Canberra Packard, 1900 TR®.

Addition of Cannabinoids or of the Derivatives According to the Present Invention During RBL-2H3 Cells Activation It was evaluated the effect Df the amidic derivatives of the invention (stock solution in DMSO) and of cannabinoids in the presence or in the absence of anandamide (stock solution in ethanol) on DNP-HSA-induced 3H-serotonin release in DNP sensitized cells. To this purpose, cannabinoids or the amidic derivatives of the invention, with or without addition of anandamide, were added to the cell activation medium (PIPES±DNP-HSA) at the desired concentration. In all cases, the medium was incubated at 37° C. for 15 min, while the total final concentration was kept constant (0.2% solvents).

The amides of the invention were solubilized in 0.2% DMSO and 0.1% absolute ethanol, except for N-palmitoylethanolamide, which was solubilized in 1% DMSO and 0.1% ethanol.

Quantification of 3H-serotonin Net Release After RBL-2H3 Cells Activation 3H-serotonin release in the various samples was calculated according to the following formula:

$$release = \frac{dpm\ released}{(dpm\ released + dpm\ associated\ with\ the\ cells)} \times 100$$

where "dpm" indicates nuclear disintegrations per minute.

The effect of the amides of the invention was expressed as the percentage of 3H-serotonin net release (i.e. after deduction of the percentage of release in the absence of DNP-HSA) or as the percentage of 3H-serotonin release inhibition.

The results of evaluation tests on the functional effects of cannabinoids and of the amidic derivatives of the invention are shown in Table 2. These data indicate that natural cannabinoids Δ8-tetrahydrocannabinol (Δ8-THC) and Δ9-tetrahydrocannabinol (Δ9-THC), the synthetic cannabinoid Nabilone and the labelled receptor agonist WIN 55,212-2 are able to inhibit, in a concentration-dependent way, RBL cells immunogenic activation measured as serotonin release. The compounds described in Examples 1, 25 and 27 can inhibit the effects induced by mast cell activation and exert an effect that is higher than or comparable to the one of cannabinoids.

Conversely, anandamide and the compounds described in Examples 19 and 28 are unable to affect serotonin release, like N-(2-hydroxyethyl)-linoleylamide, having two double bonds in the acyl portion and reported in Table 3 by way of comparison. Said data demonstrate a specific structural selectivity in the receptor functional activation:

the compounds derived from saturated carboxylic acids are more potent in exerting the functional effects following receptor activation.

Table 3

Effect of natural and synthetic cannabinoids and of the amides according to the present invention on serotonin release induced by ADNP/DNP.HSA immunogenic stimulation in RBL-2H3 cells. The compounds were solubilized in 0.1% DMSO and 0.1% ethanol.

| Molecules added after sensitization with ADNP | [3H]serotonin net release (%) | ED50 ($\mu$m) |
|---|---|---|
| DNP.HSA- | 100 | |
| DNP.HSA + WIN 55,212-2 (50 $\mu$M) | 0 | 6.4 |
| DNP.HSA + Nabilone (10 $\mu$M) | 0 | 2.8 |
| DNP.HSA + $\Delta$8-THC (25 $\mu$M) | 0 | 5 |
| DNP.HSA + $\Delta$9-THC (25 $\mu$M) | 27 | 5 |
| DNP.HSA + 11-nor-$\Delta$8-THC-9 (20$\mu$M) | 33 | 15 |
| DNP.HSA + anandamide | 100 | — |
| DNP.HSA + Example 1 (3 $\mu$M) | 0 | 0.6 |
| DNP.HSA + Example 9 (100 $\mu$M) | 0 | — |
| DNP.HSA + Example 10 (100 $\mu$M) | 0 | — |
| DNP.HSA + Example 19 (100 $\mu$M) | 100 | — |
| DNP.HSA + Example 24 (60 $\mu$M) | 67 | — |
| DNP.HSA + Example 25* (10 $\mu$M) | 0 | 2.6 |
| DNP.HSA + Example 26 (50 $\mu$M) | 21 | 28 |
| DNP.HSA + Example 27 (7.5 $\mu$M) | 0 | 3.8 |
| DNP.HSA + Example 28 (100 $\mu$M) | 100 | — |
| DNP.HSA + Example 36 (100 $\mu$M) | 51 | — |
| DNP.HSA + Example 39 (50 $\mu$M) | 68 | — |
| DNP.HSA + N-(2-hydroxyethyl)-linoleylamide (100 $\mu$M) | 100 | — |

* At the concentration used (minimum effective concentration), the compound, depending on its solubility limit, was solubilized in 1% DMSO and 0.1% ethanol. At said concentration, DMSO reduces the immunogenic stimulus potency by at least 50%.

Co-incubation of anandamide with natural or synthetic cannabinoids and with the derivatives described in Examples 1, 9, 10, 24–27, 36 and 39 reduces the ability of the amides of the invention, as well as of cannabinoids, to inhibit serotonin release, as reported in Table 4.

Table 4

Anandamide antagonism towards the inhibitory effect of cannabinoids and amidic derivatives of the invention on ADNP/DNP.HSA-induced activation in RBL-2H3 cells.

| Molecules added after sensitization with ADNP | 3H-serotonin net release inhibition (%) | |
|---|---|---|
| | − anandamide | + anandamide (12.5 $\mu$M) |
| DNP.HSA + WIN 55,212-2 (30 $\mu$M) | 100 | 36 |
| DNP.HSA + Nabilone (5 $\mu$M) | 90 | 50 |
| DNP.HSA + $\Delta$8-THC (25 $\mu$M) | 100 | n.d. |
| DNP.HSA + $\Delta$9-THC (25 $\mu$M) | 73 | n.d. |
| DNP.HSA + 11-nor-$\Delta$8-THC-9 (20 $\mu$M) | 67 | n.d. |
| DNP.HSA + Example 1 (3 $\mu$M) | 100 | 39 |
| DNP.HSA + Example 25 (10 $\mu$M)* | 100 | 0 |
| DNP.HSA + Example 26 (50 $\mu$M) | 79 | 48 |
| DNP.HSA + Example 27 (7.5 $\mu$M) | 100 | 46 |

* At the concentration used (minimum effective concentration), the compound, depending on its solubility limit, was solubilized in 1% DMSO and 0.1% ethanol. At said concentration, DMSO reduces the immunogenic stimulus potency by at least 50%.

The data reported in Table 5 show that the co-incubation of anandamide with natural or synthetic cannabinoids and with the amidic derivatives according to the present invention reduces the potency of anandamide, indicating that anandamide causes a competitive antagonism on the peripheral receptor. Therefore, as shown in Table 1, anandamide, though having binding affinity for the peripheral receptor, is not able to induce biological effects and, by competing for the receptor, functionally are recognizes the protective effects of cannabinoids.

Table 5

ED$_{50}$ of cannabinoids and of the amidic derivatives of the invention on the inhibition of 3H-serotonin release induced by ADNP/DNP.HSA stimulation in RBL-2H3 cells, in the presence and in the absence of anandamide.

| | ED50 ($\mu$M) | |
|---|---|---|
| Molecules | − anandamide | + anandamide (12.5 $\mu$M) |
| WIN 55,212-2 | 6.4 | 40 |
| Nabilone | 2.8 | 5 |
| $\Delta$8-THC | 5 | n.d. |
| $\Delta$9-THC | 5 | n.d. |
| 11-nor-$\Delta$8-THC-9 | 15 | n.d. |
| Example 1 | 0.6 | 4.0 |
| Example 12 | 1.1 | 29.0 |
| Example 23 | 2.4 | 10.1 |
| Example 25 | 2.6 | n.d. |
| Example 26 | 28 | 50 |
| Example 27 | 3.8 | 9.5 |

The competitive antagonism of anandamide on the peripheral receptor is exerted by the integral molecule and not by anandamide metabolites, as shown in Table 6.

Table 6

3H-serotonin release inhibition by WIN 55,212-2 (used at a concentration of 30 $\mu$m): antagonistic effect of anandamide vs. the metabolites of the same.

| | 3H-serotonin net release inhibition (%) | |
|---|---|---|
| | − WIN | + WIN |
| DNP.HSA | 0 | 69 |
| DNP.HSA + 12.5 $\mu$M anandamide | 7 | 15 |
| DNP.HSA + 12.5 $\mu$M ethanolamine | 6 | 72 |
| DNP.HSA + 12.5 $\mu$M arachidonic acid | 4 | 59 |

-continued

| | 3H-serotonin net release inhibition (%) | |
|---|---|---|
| | − WIN | + WIN |
| DNP.HSA + 12.5 μM ethanolamide + 12.5 μM arachidonic acid | 3 | 61 |

As a proof of the close structure-activity relationship, N-(2-hydroxyethyl)-palmitoleylamide (Example 9), like anandamide, shows a binding affinity to the peripheral receptor (as previously shown in Table 1), without exerting biological effects and, by competing for the receptor, functionally antagonizes the protective effects of cannabinoids, as reported in Table 7.

Table 7

Inhibition of 3H-serotonin release in RBL-2H3 cells, induced by ADNP/DNP-HSA stimulation caused by WIN 55,212-2: inhibitory effect of N-(-2-hydroxyethyl)-palmitoleylamide (Example 19)

| | Concentration | 3H-serotonin release inhibition (%) N-(2-hydroxyethyl)-palmitoleylamide | |
|---|---|---|---|
| | (μm) | (−) | (+) |
| WIN 55,212-2 | 5 | 8 | 8 |
| | 10 | 12 | 10 |
| | 50 | 76 | 24 |
| | 70 | 96 | 30 |
| | 100 | 98 | 56 |

The experimental data of Tables 4 and 8 show that the receptor specificity and the degree of activity are functional to the nature of both the acyl and aminic portions of the amidic derivatives according to the present invention. In fact, the experimental data show a structure-activity specificity as regards the receptor activation. In particular, said data provide evidence that saturated carboxylic acids derivatives are able to exert the most potent functional effects, whereas the presence of several unsaturation points causes the inability to functionally activate the peripheral receptor.

Table 8

Inhibitory effect of the amidic derivatives according to the present invention on 3H-serotonin release induced by ADP/DPN.HSA immunogenic stimulation in RBL-2H3 cells.

| | 3H-serotonin release inhibition % DMSO | |
|---|---|---|
| Compounds | 0.2% | 1% |
| Example 2 | 100 (100 μM) | 100 (100 μM) |
| Example 3 | 100 (100 μM) | 100 (100 μM) |
| Example 4 | 100 (100 μM) | 100 (100 μM) |
| Example 5 | 82 (30 μM) | 100 (100 μM) |
| Example 7 | 93 (30 μM) | 100 (100 μM) |
| Example 9 | 100 (100 μM) | |
| Example 12 | 86 (100 μM) | 100 (100 μM) |
| Example 13 | 65 (200 μM) | |
| Example 22 | 100 (100 μM) | 91 (100 μM) |
| Example 23 | 60 (60 μM) | 91 (100 μM) |
| Example 24 | 40 (60 μM) | 88 (100 μM) |
| Example 26 | >95%(100 μM) | >95%(100 μM) |

-continued

| | 3H-serotonin release inhibition % DMSO | |
|---|---|---|
| Compounds | 0.2% | 1% |
| Example 29 | 36 (50 μM) | 88 (30 μM) |
| Example 39 | 32 (50 μM) | 67 (100 μM) |

Numbers in paretheses are the concentrations (μM) used for the various compounds in the tests.

Table 9

Inhibition of |3H| serotonine release RBL-2H3 immunogenically stimulated. The compounds of the invention were present during the 15 minutes release period. EC50 is the concentration inhibiting by 50% the net release of |3H| serotonin from DNP-HSA-activated RBL-2H3 cells.

| | EC50 | |
|---|---|---|
| Compound | 0.2% DMSO | 1% DMSO |
| Example 2 | 1.8 | 5.0 |
| Example 3 | 1.2 | 4 |
| Example 4 | 78 | 1.05 |
| Example 5 | 8 | 7.6 |
| Example 6 | 30 | 8.8 |
| Example 7 | 4.7 | |
| Example 8 | 18 | |
| Example 11 | 26 | |
| Example 12 | 44 | 1.1 |
| Example 13 | | 32 |
| Example 18 | 63 | |
| Example 20 | 6.3 | |
| Example 21 | 1.5 | |
| Example 22 | 35 | 11 |
| Example 23 | | 11 |
| Example 24 | | 7.2 |
| Example 29 | 42 | 3.5 |
| Example 30 | 3.9 | |
| Example 31 | 7.7 | |
| Example 32 | 0.73 | |
| Example 33 | 4.7 | |
| Example 34 | 13 | 0.36 |
| Example 35 | 6.3 | 9.2 |
| Example 37 | | 15 |

The experimental data reported above prove a precise structure-activity correlation in the selective activation of CB2 peripheral receptor, which mediates the non-psychoactive effects of cannabinoids. More precisely, the molecules having a saturated acylic chain are able to bind and, above all, to functionally activate CB2 peripheral receptor to a significant extent. To the contrary, compounds with more than one double bond in the acyl chain, though having affinity to CB2 receptor, are not able to activate said receptor functionally, thus acting as partial competitive receptor antagonists.

As a proof of this structural specificity, it is known that palmitoylethanolamide, which, as demonstrated by the Applicant, is capable of functionally activating the peripheral receptor, is not able to bind to the central receptor and to mimic the cannabinoid psychoactive action, as instead do compounds having polyunsaturated acylic chain (W.A. Devane et al., Isolation and Structure of a Brain Constituent That Binds to the Cannabinoid Receptor, Science, 258: 1946–1949, 1992).

Furthermore, the aforementioned experimental results demonstrate that mast cells express the cannabinoid peripheral receptor and that the amidic derivatives according to the present invention behave as competitive agonists of CB2 receptor with an affinity that is higher than, or in any case comparable with the one of natural and synthetic cannabinoids. Moreover, they functionally activate said receptor.

Importantly, the Applicant has found that also non-immune cells functionally express cannabinoid peripheral receptor CB2, which was observed for example in cerebellar granule cells, cerebellum, heart and lung.

Said results are extremely interesting from a therapeutic point of view: in fact, the amides of the invention are suitable for the treatment of all diseases for which cannabinoids are notoriously efficacious, acting only on CB2 peripheral receptor and excluding the activity mediated by CB1 central receptor, responsible for untoward effects, such as for example habit and addiction.

In other words, thanks to their specific characteristics, the amidic derivatives of the invention are able to selectively bind and to functionally activate CB2 cannabinoid peripheral receptor. Therefore, they constitute an important therapeutic tool for the treatment of the diseases connected with an anomalous modulation of CB2 cannabinoid peripheral receptor or profiting by the activation of said receptor with consequent negative modulation of cytotoxic or proinflammatory phenomena, or, in any case connected with cytokine, neurokine or enzyme release, or with second messenger activation.

Therefore, said compounds are particularly useful in the therapeutic treatment of diseases connected with the modulation of said receptor, such as:

diseases with nociception alteration;
  muscular spasm connected with degenerative diseases of the nervous system, such as multiple sclerosis and amyotrophic lateral sclerosis;
  diseases connected with the immune system alteration;
  diseases involving pressure alterations (hypertension) at cardiovascular, polmunary and ocular levels, glaucoma and cephalea;
  nausea, also of iatrogenic nature;
  pathologies caused by biological agents, such as viral (HIV) and bacterial encephalitic meningitis, bacterial meningitis and meningitis by cytomegalovirus;
  cachetic symptomatology associated with chronic degenerative pathologies such as senile dementia, Alzheimer's and Parkinson's diseases;
  cardiovascular pathologies associated with vascular remodelling, i.e. restenosis after angioplasty including stent application, atherosclerosis and heart attack;
  Chronic airway obstruction including asthma.

In view of their effects, the amidic derivatives according to the present invention are suitable for the therapeutic treatment of human and animal diseases.

For all aforesaid diseases, the systemic administration of the claimed compounds by the oral or parenteral or topical or transdermic ways may be envisaged.

The therapeutically effective dose varies depending on the way of administration and on the method of application as well as on the disease seriousness. It also varies depending on the patient's age, weight and general health conditions. In any case, acceptable therapeutic doses may range from 0.1 to 20 mg/kg/die, preferably from 0.3 to 10 mg/kg/die, over variable periods in any case for at least 30 days.

The pharmaceutical compositions containing as the active principles the amides according to the present invention are inclusive of all formulations containing pharmaceutically acceptable excipients, that are suitable for the administration of the active ingredients in the forms best suited to the disease to be treated and, in any case, rendering the active ingredient as bioavailable as possible.

In particular, solutions or suspensions for general i.v., s.c. and i.m. administration, solutions for ophthalmic treatment in the form of eyewash, solid or semisolid formulations in the form of inserts, gels and ointments are to be envisaged. As concerns oral formulations, granular powders, tablets, pills and capsules will be preferred. As concerns dermic and transdermic administration, creams, ointments, gels and plasters, where the active ingredient may be included in slow-releasing microspheres, will be preferred.

The following examples, reported by way of indication, not of limitation, of the present invention, are meant to provide evidence of possible industrial applications of the invention.

EXAMPLE 40

Vials For Injection
  Every vial contains:
  Compound of Example 9 20 mg
  Mannitol 12 mg
  Sodium metasulphite 1.3 mg
  Benzyl alcohol 80 mg
  Propylene glycol 400 mg
  Sodium hydroxide q.s. to pH 7
  Water for injectable formulations q.s. to 2 ml

EXAMPLE 41

Tablets
  Every tablet contains:
  Compound of Example 9 50 mg
  Dibasic dehydrated calcium phosphate 135.2 mg
  Microgranular cellulose 36 mg
  Maize starch 7.2 mg
  Magnesium stearate 1.8 mg
  Hydrogenated vegetable oil 1.2 mg
  Precipitated silica 0.6 mg
  Hydroxypropylene ethylcellulose 4.7 mg
  Titanium dioxide 0.3 mg

EXAMPLE 42

Eyewash
  Every bottle contains:
  Compound as per Example 27 25 mg
  Borax 15 mg
  Boric acid 75 mg
  Polysorbate 80 15 mg
  Lactose 80 mg
  Phenol 3.9 mg
  Disodium edetate 5 mg
  Water for injectable formulation q.s. to 5 ml

EXAMPLE 43

Soft Capsules
  Every capsule contains:
  Compound of Example 1 100 mg
  Excipient: peanut oil O.P. 100 mg
  Composition of the capsule:
  gelatin O.P., glycerin O.P., natural dye E12.

What is claimed is:

1. A therapeutic method of modulating CB2 cannabinoid peripheral receptor in humans or animals, comprising administering to said humans and animals a therapeutically effective amount of at least one amide of formula (I):

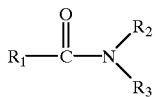

(I)

wherein $R_2$ and $R_3$ belong to one of the following classes A–C:

Class (A) when $R_2$ us a linear or branched hydroxyalkyl containing 1 to 20 carbon atoms, optionally substituted with one or more phenyl groups: then $R_3$ is H, $CH_3$ or=$R_2$;

Class (B) when $R_2$ is an alkylene-hydroxyphenyl, the aromatic ring being optionally substituted with at least one member selected from the group consisting of —OH, —$OCH_3$ and combinations thereof and the linear or branched alkylene chain containing 1 to 20 carbon atoms; then $R_3$, with the nitrogen atom to which said two substituents are linked, form a cyclic amino-ether containing 5 to 7 carbon atoms, optionally substituted with linear or branched alkyl groups; wherein for each of Classes A–C the alcoholic function —OH can be optionally replaced by —OX, where X is selected from the group consisting of any acyl, an O-phosphate, and the emiacyl of a bicarboxylic acid;

and wherein $R_1$ is defined as follows:
(1) $R_1$ a linear or branched hydrocarbon radical containing 9 to 23 carbon atoms, either saturated or containing one double bond, optionally substituted with one or more —OH groups; or
(2) $R_1$ is a group of formula (II)

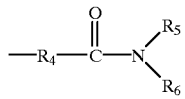

(II)

where $R_4$ is a linear or branched hydrocarbon radical containing 8 to 22 carbon atoms, either saturated or containing one double bond, optionally substituted with one or more —OH groups, with the proviso that $R_4$ is neither azelaic acid or traumatic acid; and $R_5$ and $R_6$ being defined as $R_2$ and $R_3$ respectively.

2. The therapeutic method according to claim 1, wherein, when $R_1$ is defined as in (1), it is a hydrocarbon radical containing 11 to 17 carbon atoms.

3. The therapeutic method according to claim 1, wherein, when $R_1$ is as defined in (2), $R_4$ is a hydrocarbon radical containing 10 to 16 carbon atoms.

4. The therapeutic method according to claim 1, wherein, when $R_1$ is as defined in (1), it forms, with the adjacent carbonyl, the acyl of a monocarboxylic acid selected from the group consisting of lauric, myristic, plamitic, stearic, plamitoleic, oleic and ω-hydroxyplamitic acids.

5. The therapeutic method according to claim 1, wherein, when $R_2$ and $R_3$ belong to class (A), $R_2$ forms, with the nitrogen atom to which it is linked, the residue of monoethanolamine, diethanolamine, 2-hydroxy-propyl-amine or di-(2-hydroxy-propyl)-amine.

6. The therapeutic method according to claim 1, wherein, when $R_2$ and $R_3$ belong to class (B), $R_2$ forms, with the nitrogen atom to which it is linked, the residue of tyramine or 4-hydroxy-3-methoxy-benzylamine.

7. The therapeutic method according to claim 1, wherein, when $R_2$ and/or $R_3$ belong to class (C), $R_2$ and $R_3$ form, with the nitrogen atom to which it is linked, the residue of morpholine.

8. The therapeutic method according to claim 1, characterised in that, when X is an acyl, it is —CO—$CH_3$ or —CO—Ph.

9. The therapeutic method according to claim 1, wherein, when X is an O-phosphate, it is —$PO_3H_2$ or —$PO_2H$—O—$CH_2$—CH(OH)—$CH_2$—OH.

10. The therapeutic method according to claim 1, wherein, when X is the emiacyl of a bicarboxylic acid, it is —CO—$CH_2$—$CH_2$—COOH or —CO—$(CH_2)_3$—COOH.

11. The therapeutic method according to claim 1, wherein X is salified with the ions of K, Na, Mg or Ca.

12. The therapeutic method according to claim 1, wherein said amide of formula (I) is administered at a dosage ranging from 0.1 to 20 mg/kg/die, for at least 30 days.

13. The therapeutic method according to claim 12, wherein said amide of formula (I) is administered at a dosage ranging from 0.3 to 10 mg/kg/die.

14. The therapeutic method according to claim 1, wherein said amide of formula (I) is orally, parenterally, topically or transdermically administered.

15. The therapeutic method according to claim 14, wherein said amide of formula (I) is parenterally administered by i.v., s.c. or i.m. routes, in the form of a solution or suspension.

16. The therapeutic method according to claim 14, wherein said amide of formula (I) is topically administered in the form of eyewash for ophtalmic use, or in a solid or semisolid formulation, insert, gel or ointment.

17. The therapeutic method according to claim 14, wherein said amide of formula (I) is orally administered in the form of a granular powder, tablet, pill or capsule.

18. The therapeutic method according to claim 14, wherein said amide of formula (I) is topically or transdermically administered, in the form of cream, ointment, gel or plaster, said active ingredient being optionally included in slow-releasing microspheres.

* * * * *